(12) United States Patent
Stikeleather

US012358947B2

(10) Patent No.: US 12,358,947 B2
(45) Date of Patent: Jul. 15, 2025

(54) METHOD FOR AUTOMATED PROTEIN PURIFICATION

(71) Applicant: Ryan Stikeleather, Phoenix, AZ (US)

(72) Inventor: Ryan Stikeleather, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1003 days.

(21) Appl. No.: 17/242,973

(22) Filed: Apr. 28, 2021

(65) Prior Publication Data

US 2021/0355161 A1 Nov. 18, 2021

Related U.S. Application Data

(60) Provisional application No. 63/024,050, filed on May 13, 2020.

(51) Int. Cl.
*C07K 1/36* (2006.01)
*C07K 1/22* (2006.01)

(52) U.S. Cl.
CPC . *C07K 1/36* (2013.01); *C07K 1/22* (2013.01)

(58) Field of Classification Search
CPC ....................................................... C07K 1/22
See application file for complete search history.

(56) References Cited

U.S. PATENT DOCUMENTS

2004/0033530 A1 2/2004 Awrey et al.
2015/0299637 A1* 10/2015 Park ................. C12M 23/12
435/68.1

OTHER PUBLICATIONS

Chen, Shi, et al. "Two-step magnetic bead-based (2MBB) techniques for immunocapture of extracellular vesicles and quantification of microRNAs for cardiovascular diseases: A pilot study." PLoS One 15.2 (2020): e0229610. (Year: 2020).*
A Beginner's Guid to Tag-Removing Proteases; BiteSizeBio; Sep. 28, 2016; https://bitesizebio.com/30294/beginners-guide-tag-removing-proteases/ (Year: 2016).*
PreScission Protease 2012; https://us.vwr.com/assetsvc/asset/en_US/id/15167465/contents (Year: 2012).*
Nomura, Yayoi, et al. "The intervening removable affinity tag (iRAT) production system facilitates Fv antibody fragment-mediated crystallography." Protein Science 25.12 (2016): 2268-2276. (Year: 2016).*
Shin et al., "Synthesis of Fe3O4@nickel-silicate core-shell nanoparticles for His-tagged enzymes immobilizing agents", Nanotechnology 27: 495705 9 pages (Year: 2016).*
Raran-Kurussi and Waugh, "A dual protease approach for expression and affinity purification of recombinant proteins", Analytical Biochemistry 504: 30-37 (Year: 2016).*
Magne HaloTag Beads Technical Manual (2015), Promega Corporation.
HaloTag Protein Purification System Technical Manual (2017), Promega Corporation.
Altschul et al. "Basic Local Alignment Search Tool" (1990) J. Mol. Biol. 215:403-410
Altschul et al. "Gapped BLAST and PSI-BLAST: a new generation of protein database search programs" (1997) Nucleic Acids Res. 25:3389-402.
Gonnet et al. "Exhaustive Matching of the Entire Protein Sequence Database" (1992) Science 256: 1443-1445.

* cited by examiner

*Primary Examiner* — Anand U Desai
(74) *Attorney, Agent, or Firm* — FULLER IP LAW LLC; Rodney J. Fuller

(57) ABSTRACT

Methods and systems for automated protein purification are disclosed. The disclosed methods and systems utilize a plurality of magnetic bead chemistries and an automated extraction system for the purification of one or more proteins within a short time frame.

10 Claims, 27 Drawing Sheets

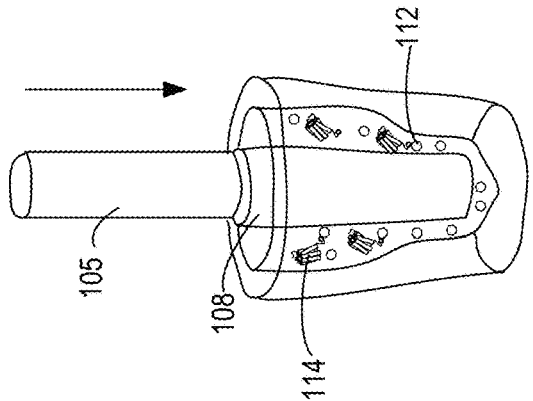

FIG. 1A — Mixing of magnetic beads with sample to bind to target

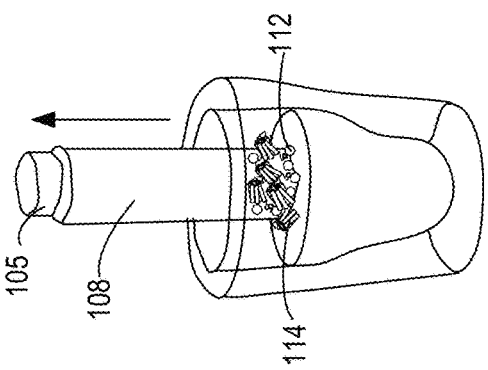

FIG. 1B — Lower magnetic rod into solution where magnetic beads and target collect at bottom of tip comb

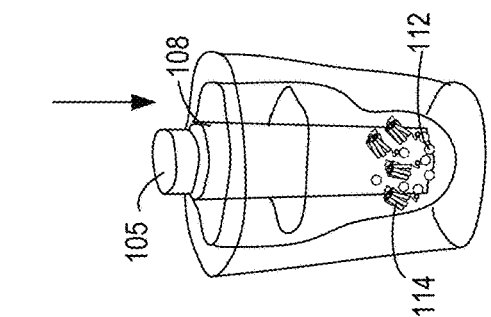

FIG. 1C — Retraction of magnetic rod. Beads and target can be positioned in another well.

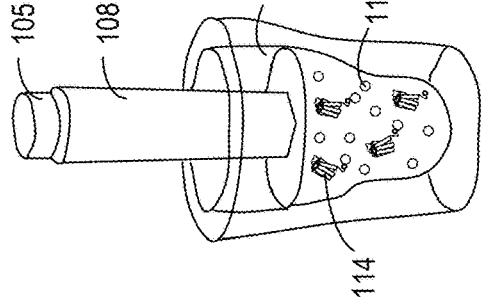

FIG. 1D — Release of beads by moving magnetic rod out of tip comb. Tip comb also can be used to mix reagents with beads as magnetic head moves up and down

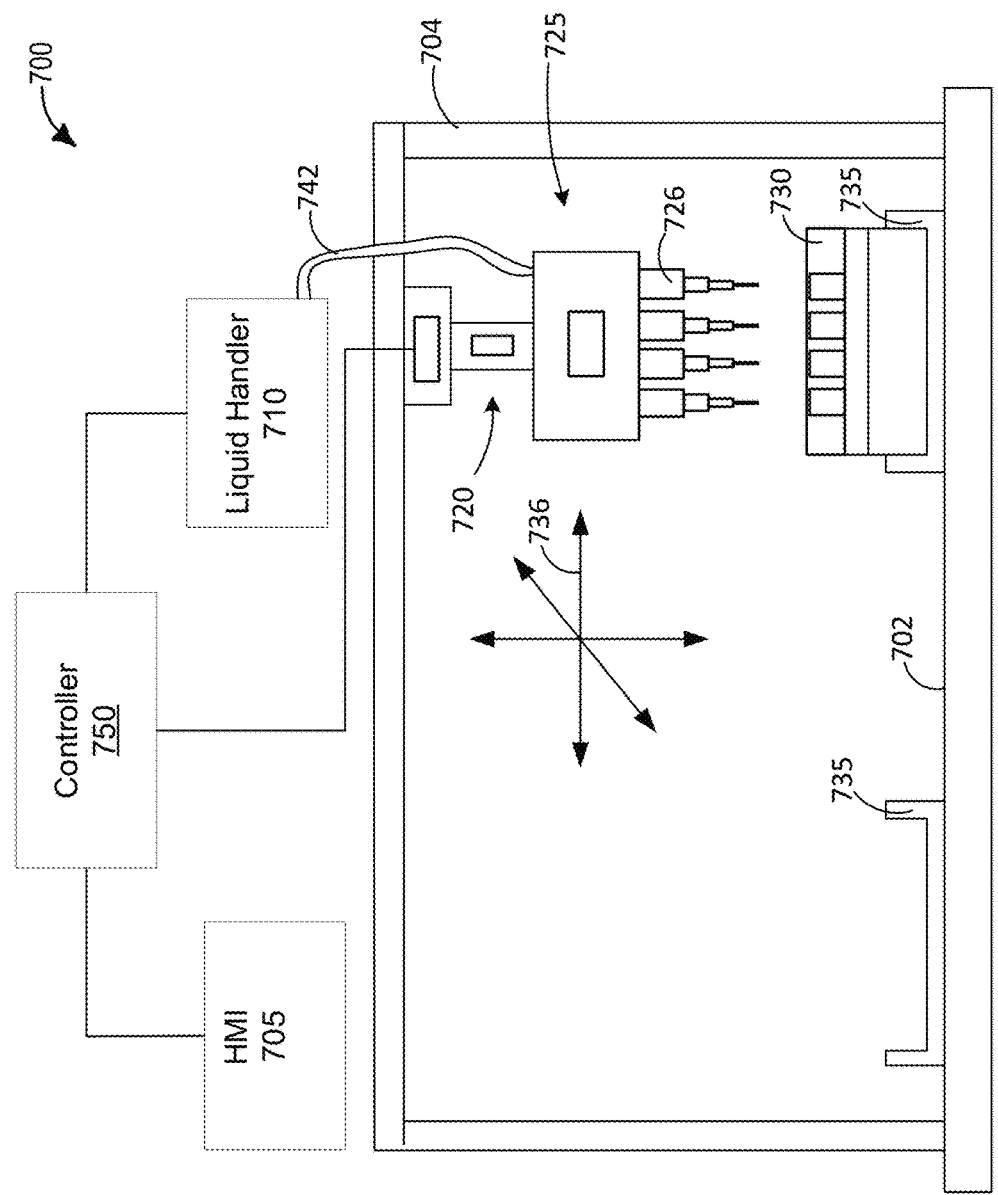
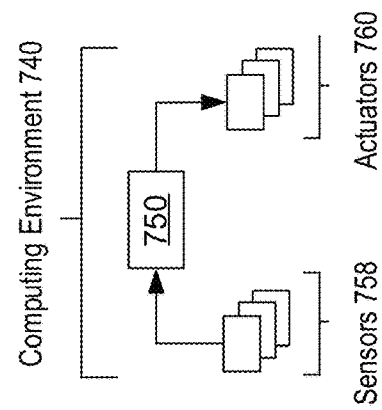
FIG. 7

| Strain Number | Protein | Mass (kDA) |
|---|---|---|
| RS-126 | holE | 8.8 |
| RS-79 | holE-dnaQ | 8.8 + 27.1 = 35.9 |
| RS-130 | dnaE-holE-dnaQ | 129.9 + 8.8 + 27.1 = 165.8 |

METHOD FOR AUTOMATED PROTEIN PURIFICATION

CROSS-REFERENCE TO RELATED APPLICATIONS

This application claims the priority benefit of the earlier filing date of U.S. Provisional Application No. 63/024,050, filed May 13, 2020, which is hereby incorporated by reference in its entirety.

GOVERNMENT SUPPORT CLAUSE

This invention was made with government support under W911 NF-14-1-0411 awarded by the Army Research Office. The government has certain rights in the invention.

FIELD

This disclosure relates to protein purification and in particular, to methods and systems for automated protein purification.

BACKGROUND

Purifying proteins is often a long, tedious procedure which even at the end of the process often results in only partially purified product. For example, purification of protein by hand can involve numerous centrifugation steps and pipette motions, each of which take time, energy, and have the potential for human error. In the case of stationary magnet systems, there is one step of centrifugation, and over twenty pipette motions again. For both types of procedures, pipetting is performed in the presence of beads which can lead to both product loss and lower quality purifications. The current protein purification methods suffer from inefficiency, lack of reproducibility and relatively dirty purified product.

SUMMARY

Disclosed herein are automated methods and systems for protein purification. In one aspect, a method for automated purification of a target protein, comprises contacting a sample with one or more type 1 magnetic beads under conditions sufficient for the one or more type 1 magnetic beads to bind to the target protein in the sample, washing the one or more type 1 magnetic beads to remove contaminating material from the sample, contacting the sample with a cleavage solution containing a protease to release the target protein from the one or more type 1 magnetic beads, contacting the sample with one or more type 2 magnetic beads under conditions sufficient to bind the protease in the sample, and removing the one or more type 1 magnetic beads and the one or more type 2 magnetic beads, thereby purifying the target protein.

In embodiments, washing the one or more type 1 magnetic beads further comprises contacting the one or more type 1 magnetic beads that are bound to the target protein with a magnet under conditions sufficient to bind the one or more type 1 magnetic beads to the magnet, transferring the one or more type 1 magnetic beads that are bound to the target protein to one or more wash solutions to facilitate removal of contaminating material from the sample, and subsequent to the washing, releasing the one or more type 1 magnetic beads from the magnet.

In embodiments, the method further comprises removing the one or more type 1 magnetic beads from the sample prior to contacting the sample with the one or more type 2 magnetic beads.

In embodiments, contacting the sample with the one or more type 2 magnetic beads occurs without prior removal of the one or more type 1 magnetic beads from the sample.

In embodiments, the one or more type 1 magnetic beads bind to the target protein by way of a first affinity tag, and the protease cleaves the target protein from the first affinity tag, thereby releasing the target protein from the one or more type 1 magnetic beads while the first affinity tag remains bound to the one or more type 1 magnetic beads.

In embodiments, the one or more type 2 magnetic beads bind to the protease by way of a second affinity tag. In an example, the first affinity tag and the second affinity tag are different. In an example, the first affinity tag and the second affinity tag are different.

In embodiments, the target protein is comprised of two or more different proteins, and wherein the protease further cleaves the target protein into the two or more different proteins.

In embodiments, the method does not include any centrifugation steps.

In embodiments, the method does not involve the use of any detergent.

In an aspect, an automated protein purification method comprises contacting a sample with one or more type 1 magnetic beads under conditions sufficient for the one or more type 1 magnetic beads to non-covalently bind to the target protein in the sample; washing and eluting the target protein from the one or more type 1 magnetic beads, followed by removal of the one or more type 1 magnetic beads; contacting the sample with one or more type 2 magnetic beads under conditions sufficient for the one or more type 2 magnetic beads to covalently bind to the target protein in the sample; contacting the sample with a cleavage solution containing a protease to release the target protein from the one or more type 2 magnetic beads; contacting the sample with one or more type 3 magnetic beads under conditions sufficient to bind the protease in the sample; and removing the type 2 and the type 3 magnetic beads, thereby purifying the target protein.

In embodiments, the one or more type 1 magnetic beads bind to the target protein by way of a first affinity tag, wherein the one or more type 2 magnetic beads bind to the target protein by way of a second affinity tag. In examples, the first affinity tag and the second affinity tag are different.

In embodiments, the first affinity tag and the second affinity tag are on the same terminus of the target protein. In such an embodiment, the protease releases the target protein from the one or more type 2 magnetic beads in a manner that cleaves both the first affinity tag and the second affinity tag from the target protein, thereby maintaining the first affinity tag and the second affinity tag attached to the one or more type 2 magnetic beads following release of the target protein from the one or more type 2 magnetic beads.

In embodiments, the target protein further comprises a third affinity tag on an opposing terminus as that of the first affinity tag and the second affinity tag. In such an embodiment, the automated protein purification method further comprises following removal of the one or more type 1 magnetic beads and prior to contacting the sample with the one or more type 2 magnetic beads, contacting the sample with one or more type 4 magnetic beads to non-covalently bind the target protein in the sample by way of the third affinity tag, and washing and eluting the target protein from the one or more type 4 magnetic beads, followed by removal of the one or more type 4 magnetic beads. In examples, the protease further releases the target protein from the third affinity tag. In examples, contacting the sample with the one or more type 3 magnetic beads under conditions sufficient to bind the protease in the sample further comprises contacting the sample with the one or more type 4 magnetic beads under conditions sufficient to bind the third affinity tag. In examples, removing the type 2 and the type 3 magnetic beads further comprises removing the type 4 magnetic beads.

In embodiments, the first affinity tag and the second affinity tag are on opposing termini of the target protein. In examples, the protease releases the target protein from the one or more type 2 magnetic beads in a manner that cleaves both the first affinity tag and the second affinity tag from the target protein, wherein just the second affinity tag remains attached to the one or more type 2 magnetic beads. In examples, following release of the target protein from the one or more type 2 magnetic beads, the method may further comprise contacting the sample with the type 1 magnetic beads under conditions sufficient to bind the first affinity tag, and wherein removing the type 2 and the type 3 magnetic beads further includes removing the type 1 magnetic beads.

In embodiments, the target protein is comprised of two or more different proteins, wherein the protease further cleaves the target protein into the two or more different proteins.

In an aspect a system for automated purification of a target protein, comprises one or more magnetic rods moveable in at least a vertical direction with respect to a platform, the platform including one or more plate holders for plates comprised of one or more wells; one or more tip combs for insertion of the one or more magnetic rods thereto; and a first type of one or more magnetic beads and a second type of one or more magnetic beads. The system may further include a controller storing instructions in non-transitory memory that, when executed, cause the controller to equilibrate each of the first type of one or more magnetic beads and the second type of one or more magnetic beads; collect the first type of one or more magnetic beads and combine the first type of one or more magnetic beads with a cell lysate including a polypeptide comprised of a target protein, a linker region recognizable by a protease, and a first affinity tag, under conditions sufficient to result in binding of the polypeptide to the first type of one or more magnetic beads; conduct one or more wash steps by collecting and transferring the first type of one or more magnetic beads bound to the polypeptide into one or more wash solutions; transfer the first type of one or more magnetic beads bound to the polypeptide into a cleavage solution containing the protease to release the target protein from the first type of one or more magnetic beads; perform a pause step to enable a user to add the second type of one or more magnetic beads to a solution containing at least the released target protein and the protease; and collect and remove the first type of one or more magnetic beads and the second type of one or more magnetic beads from the solution, thereby purifying the target protein.

In an embodiment, the first type of one or more magnetic beads includes a first recognition element that covalently binds the first affinity tag.

In an embodiment, the second type of one or more magnetic beads includes a second recognition element that either covalently or non-covalently binds a second affinity tag included as part of the protease.

The foregoing and other features of the disclosure will become more apparent from the following detailed description, which proceeds with reference to the accompanying figures.

BRIEF DESCRIPTION OF DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 1A-1D depict various stages associated with a magnetic bead mover system in accordance with various embodiments disclosed herein.

FIG. 7 depicts an automated liquid handling system in accordance with embodiments of the present disclosure.

DETAILED DESCRIPTION OF DISCLOSED EMBODIMENTS

Figure 2:
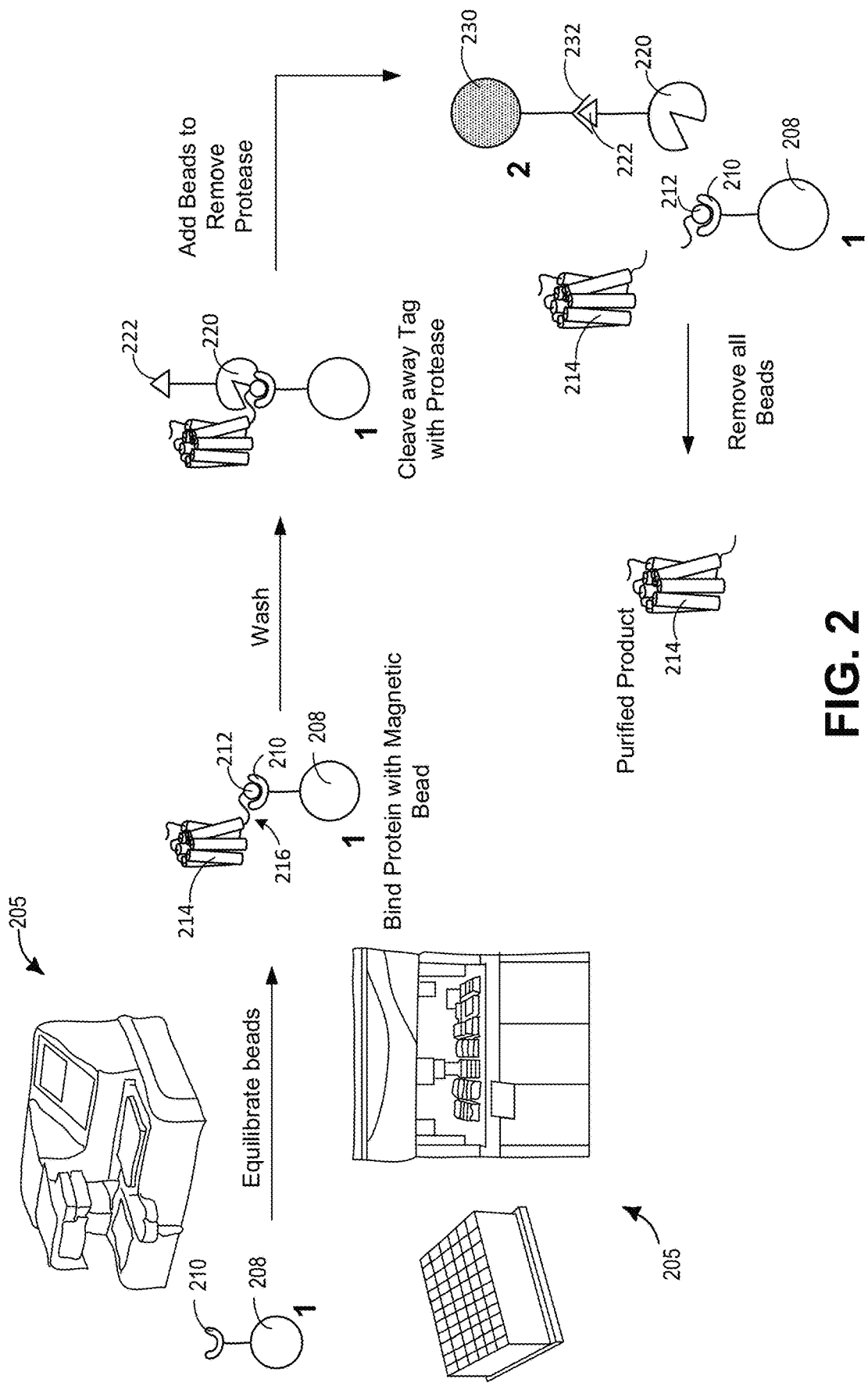
FIG. 2 illustratively depicts a method for purification of a target protein via the use of a dual magnetic bead strategy as according to embodiments.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook el al., *Molecular Cloning: A Laboratory Manual, 2d ed.*, Cold Spring Harbor Laboratory Press, 1989; Sambrook et al., *Molecular Cloning: A Laboratory Manual, 3d ed.*, Cold Spring Harbor Press, 2001; Ausubel el al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting. Although any methods and materials similar or equivalent to those described herein can be used in the practice or testing of the present invention, the preferred methods and materials are now described. All patents, applications and non-patent publications mentioned in this specification are incorporated herein by reference in their entireties.

I. Terms

To facilitate review of the various embodiments of the disclosure, the following explanations of specific terms are provided:

The terms "analysis" or "analyzing," as used herein, are used interchangeably and refer to any of the various methods of separating, detecting, isolating, purifying, solubilizing, detecting and/or characterizing molecules of interest (e.g., polypeptides, such as antibodies) in biochemical preparations (e.g., biopharmaceutical preparations), such as antibody preparations.

"Chromatography," as used herein, refers to the process of separating a mixture, for example a mixture containing peptides, proteins, polypeptides and/or antibodies. It involves passing a mixture through a stationary phase, which separates molecules of interest from other molecules in the mixture and allows one or more molecules of interest to be isolated.

"Contacting," as used herein, includes bringing together at least two substances in solution or solid phase.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr. In one embodiment, a peptide is an antibody or fragment or part thereof, for example, any of the fragments or antibody chains listed above. In some embodiments, the peptide may be post-translationally modified. In embodiments, the protein is any polypeptide that can be expressed in an expression host. For example, the polypeptide(s) that can be used with purification methodology herein disclosed can be produced using recombinant techniques. Suitable host cells for cloning and/or expression include prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis, K. bulgaricus, K. wickeramii, K. waltii, K. drosophilarum, K. thermotolerans,* and *K. marxianus; yarrowia; Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

The use of mammalian cells as hosts are also within the scope of this disclosure. Examples of useful mammalian cell lines include, but are not limited to, monkey kidney CV1 cells transformed by SV40 (COS-7, ATCC CRL 1651); human embryonic kidney cells (293 or 293 cells subcloned for growth in suspension culture, Graham et al., *J. Gen Virol.* 36:59 (1977); baby hamster kidney cells (BHK, ATCC CCL 10); Chinese hamster ovary cells/DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and human hepatoma cells (Hep G2).

"Detect" and "detection" have their standard meaning, and are intended to encompass detection including the presence or absence, measurement, and/or characterization of a protein of interest.

As used herein, the terms "protein of interest" and/or "target protein of interest", or simply "target protein" refer to any protein to be separated, purified, and/or detected with the methods, provided herein.

As used herein, the term "agent" refers to any protein, peptide, nucleic acid molecule (including chemically modified nucleic acids), compound, small molecule, organic compound, inorganic compound, or other molecule of interest.

As used herein, the term "binding" or "stable binding" refers to an association between two substances or molecules, such as the association of a protein with a magnetic bead. Binding can be detected by any procedure known to one skilled in the art including those disclosed herein, such as by physical or functional properties of the formed complexes. The protein may be bound to the magnetic bead by way of an affinity tag on the protein, recognized by a recognition element coupled to the magnetic bead. As used herein, the term "recognition element" refers broadly to any ligand or molecular structure capable of recognizing and binding to an affinity tag on a protein. Furthermore, herein the terms "magnetic bead" and "magnetic beads" are used interchangeably. As an example, a first type of magnetic bead can refer to a single first type of magnetic bead, or a plurality of the first type of magnetic bead. Generally, it may be understood that the methodology discussed herein with regards to various types of magnetic beads relies on a plurality of each type of magnetic bead.

As used herein, the term "isolated" can refer to an "isolated" biological component (such as a nucleic acid molecule, protein, or cell) that has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods, and in examples embodied herein, by the purification methodology herein disclosed. The term also embraces nucleic acid molecules and proteins prepared by recombinant expression in a host cell as well as chemically synthesized nucleic acid molecules and proteins.

As used herein, the term "label" refers to an agent capable of detection, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

As used herein, the term "optional" or "optionally" means that the subsequently described event or circumstance can but need not occur, and that the description includes instances where said event or circumstance occurs and instances where it does not.

As used herein the term "purified" does not require absolute purity; rather, it is intended as a relative term. Thus, for example, a purified protein preparation is one in which the protein referred to is more pure than the protein in its natural environment within a cell. In one example, a preparation of a single protein is purified such that the protein represents at least 50% of the total protein content of the preparation. Similarly, a purified oligonucleotide preparation is one in which the oligonucleotide is more pure than in an environment including a complex mixture of oligonucleotides. In another example, purification may comprise purification of a plurality of proteins, for example as a complex or as a single polypeptide that can be cleaved (e.g., via a protease) into the plurality of proteins. In such an example, the plurality of target proteins may represent at least 50% of the total protein content of the preparation.

Purity of a compound may be determined, for example, by high performance liquid chromatography (HPLC) or other conventional methods, including but not limited to Mass Spectrometry methodology. Compounds described herein may be obtained in a purified form or purified by any of the means known in the art, including silica gel and/or alumina chromatography. See, e.g., Introduction to Modern Liquid Chromatography, 2nd Edition, ed. by Snyder and Kirkland, New York: John Wiley and Sons, 1979, and Thin Layer Chromatography, ed. by Stahl, New York: Springer Verlag, 1969.

The terms "substantial identity" or "substantially identical" as used herein refer to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, the term "sample" refers to a mixture of molecules that includes at least one polypeptide of interest, that is subjected to manipulation in accordance with the methods of the invention, including, for example, separating, analyzing, extracting, concentrating, purifying or profiling.

As used herein, the term "standard" or "internal standard" refers to a well-characterized substance of known amount and/or identity (e.g., known molecular weight, electrophoretic mobility profile) that can be added to a sample and both the standard and the molecules in the sample, on the basis of molecular weight or isoelectric point by electrophoresis). A comparison of the standard then provides a quantitative or semi-quantitative measure of the amount of analyte, such as a protein present in the sample.

As used herein, the phrase "under conditions sufficient to" refers to any environment that permits the desired activity, such as for purifying a protein. As an example, a sample may be contacted with one or more magnetic beads under conditions sufficient for the one or more magnetic beads to bind to a target protein. As another example, a sample that includes one or more magnetic beads may be contacted by a magnetic rod under conditions sufficient for binding of the magnetic beads to the magnetic rod.

As used herein, the term "IGEPAL CA-630" is a nonionic, non-denaturing detergent. Its official IUPAC name is octylphenoxypolyethoxyethanol. IGEPAL is a registered trademark of Solvay. IGEPAL CA-630 is commercially available, such as by Sigma-Aldrich. All IGEPAL CA surfactants are derived from octylphenol. This serves as the hydrophobic part. Different amounts of ethylene oxide are combined with this part to get a balance of hydrophobic/hydrophilic substances (measured by hydrophobic-lipophilic balance, or HLB). This balance has an important impact on wetting detergency, foam, solubility, emulsification. IGEPAL CA-630 has HLB of 13.4, similar to that of Triton X-100 (13.1) and thus, belongs to the detergent range (HLB 13-15); this is significantly less than 17.8 of tergitol NP-40 or 16.7 of Polysorbate 20 (also known as Tween 20), which both belong in the solubilizer range (15-18) of HLB.

As used herein, the term "protease" refers to an enzyme whose catalytic function is to hydrolyze peptide bonds of proteins. Proteases, as herein discussed, are also referred to as proteolytic enzymes or proteinases. Proteases can differ in their ability to hydrolyze various peptide bonds. Examples of proteases relevant to the present disclosure include but are not limited to endoproteases and exoproteases. As used herein "endoprotease" refers to proteolytic peptidases that break peptide bonds of nonterminal amino acids. Alternatively, "exoprotease" refers to proteolytic peptidases that break peptide bonds from end-pieces of terminal amino acids. In general, the methods of the present disclosure employ use of endoproteases, as opposed to exoproteases.

Examples of endoproteases as herein disclosed include but are not limited to enteropeptidase, thrombin, Factor Xa, TEV protease, and human Rhinovirus 3C (HRV) Protease. Examples of exoproteases can include but are not limited to carboxypeptidase A, carboxypeptidase B, and DAPase.

"TEV protease" (Tobacco Etch Virus nuclear-inclusion-a endopeptidase) is a highly sequence-specific cysteine protease from Tobacco Etch Virus (TEV). It is a member of the PA clan of chymotrypsin-like proteases. Due to its high sequence specificity it is frequently used for the controlled cleavage of fusion proteins in vitro and in vivo.

"Enteropeptidase" is a disulfide-linked heterodimer composed of "heavy" and "light" chains (with apparent molecular weights of 110 and 35 kDa, respectively), which are extensively glycosylated. Recent advances have facilitated the production of recombinant enteropeptidase light chain in the periplasm of E. Coli, making it more economical to manufacture and yielding a product free of contaminating proteases. Moreover, the 26 kDa light chain (which, when expressed in E. coli, is devoid of glycosylation) retains the specificity of the native enzyme and is even more active on fusion protein substrates than the heterodimer.

"Thrombin" is typically purified from bovine plasma. Like many serine proteases, thrombin can be inactivated by phenylmethylsulfonyl fluoride (PMSF) or 4-(2-aminoethyl) benzenesulfonyl fluoride hydrochloride (AEBSF). Alternatively, a biotinylated form of thrombin that can be adsorbed on avidin or streptavidin resin is commercially available (Novagen, Madison, WI). Like enteropeptidase, thrombin is a disulfide-linked heterodimer. It also has three intramolecular disulfide bonds in one of its two chains, rendering it sensitive to reducing agents.

"Factor Xa" is a blood clotting enzyme like thrombin. The γ-carboxylated glycoprotein factor Xa is either isolated from blood plasma or expressed recombinantly and secreted from mammalian cells. Factor Xa is composed of two disulfide-linked polypeptide chains with apparent molecular weights of 17 and 42 kDa, each of which contains a number of internal disulfide bonds, rendering the enzyme sensitive to reducing agents. Factor Xa also binds calcium ions and therefore should not be used in the presence of chelating agents such as ethylene glycol tetraacetic acid (EGTA) and ethylenediaminetetraacetic acid (EDTA). There is some evidence of sensitivity of Factor Xa to various detergents.

"HRV protease" (Rhinovirus 3C protease) is a cysteine protease. It folds into two topologically alike six-stranded β barrels. However, β barrels are different in length and individual position as well as in loops connecting elements of secondary structure. The protease is distinguishable from others by the fact that it has a cysteine nucleophile but with a chymotrypsin-like serine protease folding.

It is within the scope of this disclosure that any of the above-mentioned proteases may be used with the methods and systems herein disclosed. This disclosure is not limited to the above-mentioned proteases, but rather, the disclosed systems and methods can be used with any protease with functional properties amenable to the present disclosure.

As used herein, the term "affinity tag" refers to a short peptide added to either the N- or C-terminus of a recombinant protein to facilitate purification of the expressed protein. Affinity tags usually contain from several to hundreds of amino acids. In some examples, affinity tags can provide additional functions unrelated to purification, such as facilitating detection of the target protein, improving solubility of the target protein, and the like.

Examples of affinity tags include but are not limited to polyhistidine tag (e.g., polypeptide consisting of several histidine residues that can be located on either the N or C-terminus of a recombinant protein, and which enables purification via affinity to metal ions including but not limited to copper, nickel, zinc, and cobalt), polyarginine tags (e.g., five or six consecutive arginines), glutathione-S-transferase (e.g., 26 kDa sequence of 211 amino acids), FLAG tag (e.g., eight amino acids with a molecular weight of 1 kDa), Streptavidin-binding peptide (SPB) (e.g., small affinity protein used as a sorbent, which can be eluted by free biotin), Strep-tag II (e.g., small affinity peptide (WSHPQFEK) that works well on both N- and C-termini of recombinant proteins), Twin-Strep Tag (e.g., consisting of two Strep-tag II moieties connected by a short linker), Calmodulin Binding Peptide (e.g., 4 kDa relatively small peptide attachable to N- and C-termini of recombinant proteins), Chitin-binding Tag (e.g., 51 amino acid chitin-binding domain that enables recombinant protein harboring the tag to bind to chitin, for example chitin immobilized on Sepharose), Maltose-binding Tag (e.g., fairly large periplasmic tag with molecular weight of 43 kDa. Amylose is used to purify proteins with maltose-binding protein), cellulose-binding tag (e.g., belongs to carbohydrate binding module family 1, and can be joined to the C- or N-terminus of a recombinant protein for use in cellulose column purification), SNAP-tag (20 kDa mutant of the DNA repair protein $O^6$-alkylguanine-DNA alkyltransferase that covalently reacts specifically and rapidly with benzylguanine (BG) derivatives), and HaloTag (e.g., approximately 33 kDa peptide derived from a bacterial enzyme, designed to covalently bind to a synthetic ligand, for example HaloTag ligand).

II. General Description

Protocols available in technical manuals involve numerous steps, such as ten steps of centrifugation and more than twenty pipette motions for by-hand protein purification procedures. For example, centrifuge steps are recommended at five minutes per spin, so this amounts to 50 minutes of extra time spent at least. In the case of stationary magnet systems, there is one step of centrifugation, but still over twenty pipette motions. For both types of procedures, pipetting is performed in the presence of beads which can lead to both product loss and lower quality purifications.

The disclosed methods and systems address the aforementioned problems associated with known manual protein purification methods. In the methods disclosed herein, sample containers, such as 96-well deep-well plates, are preloaded with the appropriate buffers, and pipetting never removes liquid from wells containing beads. Because of this, product loss and contamination is minimized. Importantly, there are no centrifugation steps, and, in embodiments, just 2 pipette motions to only add reagents. Additionally, in embodiments, these 2 pipette motions can be automated with an appropriate liquid handling robot. Because centrifugation is eliminated and pipetting is limited here, while also being the most automated, this purification method is the fastest currently available. Additionally, because only magnetic beads are used in the methods disclosed herein, detergents (e.g., IGEPAL CA-630) are not required and this allows for easy and accurate downstream quantification of purified product; this is compared to processes that include detergent (e.g., IGEPAL CA-630) in the purification buffer despite it interfering with downstream quantification.

For example, through the use of dual magnetic bead chemistries and an automated extraction system, such as the ThermoFisher KingFisher™ Flex, numerous proteins, such as up to 96 proteins, can be robotically purified from crude cell lysates. Samples can be significantly more pure when compared to a batch method completed by hand. Automating the process allows for reproducible and simultaneous purification of many proteins at once in a time efficient manner that simply is not possible when compared to methods completed by hand. As such, the disclosed methods and systems allow tagged proteins to be robotically purified from essentially crude cell extracts with far less human interaction than comparable methods, thereby providing the currently fastest way to purify proteins while increasing both the reliability and reproducibility of the process.

As such, the inventors have developed methods for automated protein purification that allow for the simultaneous and clean purification of proteins. The disclosed methods utilize a dual magnetic bead approach on an automated extraction system (i.e., bead mover system). The disclosed method can utilize any two magnetic beads (or in some examples more than two, such as three, or four, or more) for each user's specific needs. In embodiments, commercially available magnetic beads are used, such as the HaloTag® magnetic beads (Promega, Madison, WI), or Magne® Streptavidin beads (Promega, Madison, WI), or MagneGST™ (Promega, Madison, WI), or MagneHis™ (Promega, Madison WI), or Amylose Magnetic Beads (New England Biolabs, Ipswich, MA), or Streptavidin Magnetic Beads (New England Biolabs, Ipswich, MA), or Anti-MBP Magnetic Beads (New England Biolabs, Ipswich, MA), Dynabeads® and the like. Although any two magnetic beads can be used, pure agarose beads or silica-based beads may not be used in the disclosed method. It is noted that some types of agarose beads can be modified to have magnetic properties via embedding, or coating agarose with magnetite, or similar magnetic material. Those types of beads can be used in the disclosed method, but purification may suffer from protein non-specific binding to exposed agarose. Further, IGEPAL CA-630 may be required for certain magnetic agarose beads, and quantification will be adversely impacted as a result. Although these limitations may be present, the disclosed method may still offer improvement over by-hand purification, and offer improvements to speed and efficiency even if magnetic agarose beads were used in the procedure.

As discussed, the methodology herein disclosed can be used with an automated extraction system. Such as system may provide at least the following functions: incubation of reaction mixtures, mixing of reaction mixtures, separation of components from reaction mixtures, washing of reaction product(s), and the like. An automated extraction system that can be modified for use herein is a KingFisher™ magnetic particle processor, commercially available from Thermo Fisher Scientific, Inc., Waltham, Mass., and as described in the U.S. application Ser. No. 11/923,828, filed Oct. 25, 2007, and entitled METHOD OF PERFORMING ULTRA-SENSITIVE IMMUNOASSAYS, incorporated herein by reference. Other magnetic particle processors that can be modified for use in certain embodiments described herein include KingFisher™ 96 magnetic particle processor, commercially available from Thermo Fisher Scientific, Inc., Waltham, Mass. The KingFisher™ Flex magnetic particle processor can provide rapid and reproducible purification of high-quality DNA, RNA, proteins, and cells from various starting materials, such as, for example, blood, cell cultures, tissue lysates, soil, etc. Like the KingFisher™ magnetic particle processors described previously, the KingFisher™ Flex magnetic particle processor uses magnetic rods that move particle through the various purification phases, i.e., binding, missing, washing, elution. The KingFisher™ Flex magnetic particle processor uses a 24-rod magnet head and 24-well deep well plate. The volume of sample can be as high as 5 mL. For higher throughput needs, 96 samples can be processed in different working volumes (20-1000 μL) using 96-rod magnet head and appropriate 96-well plates. Details relating to the KingFisher™ Flex magnetic particle processor are accessible by means of the Hypertext Transfer Protocol on the World Wide Web at the website thermo.com/com/cda/product/detail/1,10136240,00.html, incorporated herein by reference.

Briefly, turning to FIGS. 1A-ID, the principle of operation of the automated extraction system (e.g., KingFisher™ Flex magnetic particle processor) used in the methodology herein disclosed is based on the use of magnetic rods 105 that can be covered with the tips or sheaths of disposable tip combs 108 and microwell or deepwell plates (not shown but see "wells" 110). New tip combs 108 are installed prior to processing each microwell plate. A tip comb 108 comprises a strip of non-magnetic material, which tips, or sheaths, cover the magnetic rods 105. Commercially available tip combs comprise 12 tips for the KingFisher™ magnetic particle processor and 96 tips for the KingFisher™ 96 magnetic particle processor. The magnetic particle processor is capable of functioning without any aspirating and/or dispensing devices or components. Dimensions of wells 110 are compatible with the dimensions of the tip comb 108 and the tips, or the sheaths, thereof, with the result that the tips can be used to mix or agitate the contents of the wells 110.

The operating principle employed by the magnetic particle processor is inverse magnetic particle processing technology. Rather than moving liquids from one well to another well, magnetic particles are transferred with the aid of magnetic rods 105 covered with the disposable, specially designed plastic tip combs 108. Briefly, as shown at FIG. 1A, magnetic beads 112 capable of recognizing and binding to a target 114 (e.g., target protein) that includes an affinity tag are mixed together to enable the binding. Next, as shown at FIG. 1B, the magnetic rod 105 is lowered into the solution, where the magnetic beads 112 and target 114 collect at the bottom of the tip comb 108. As shown at FIG. 1C, with the magnetic beads 112 attracted to the magnetic rod 105, retraction of the magnetic rod 105 carries with it the magnetic beads 112 and target 114. This enables the magnetic beads 112 and bound target 114 to be positioned in another well. As shown in FIG. 1D, by moving the magnetic rod 105 out of the tip comb 108, the magnetic beads 112 (and target 114) can be released, for example into a new well. The tip comb 108 can also be used to mix reagents with magnetic beads 112 and target 114. For example, magnetic particles may be release by moving the tip comb 108 up and down several times at a considerably high speed until all the magnetic beads 112 have been mixed with the contents located in the new well. Washing the magnetic particles is a frequent and important phase of magnetic particle processing activity. Washing may be understood to comprise a combination of the release step (FIG. 1D) and the collection step (FIGS. 1B-1C) in a well filled with washing solution. To maximize washing efficiency in wells of the multi-well plate (not shown), the magnetic rods 105 together with the tip comb 108 are designed to have minimized liquid-carrying properties. To keep the suspension containing the magnetic particles evenly mixed in longer-running reactions, the tip comb 108 can be moved up and down from time to time.

Thus, the automated extraction system, also referred to herein as a bead mover system, as herein discussed and for use with the methodology herein disclosed, such as the KingFisher™ Flex, is a machine that uses a magnetic plate header to transfer (e.g., 'fish') beads out of wells/plates and move them to the next well/plate. In embodiments, each plate is preloaded with the appropriate buffer, and beads are mixed, incubated, released, and in some examples heated or cooled, as programmed in the software. Both bead equilibration and protein purification according to the methods disclosed herein were adapted to the KingFisher™ Flex.

Methods for Automated Protein Purification

Turning to FIG. 2, in an embodiment, a method for automated protein purification as herein disclosed relies on an automated extraction system 205 to purify a recombinantly expressed protein from a crude cell lysate. The automated extraction system 205 may be, for example, a KingFisher™ Flex, as discussed above, which operates on the general principles outlined at FIGS. 1A-1D. Automated extraction system 205 is not shown at a high level of detail at FIG. 2, but rather is schematically illustrated for reference. In embodiments, a liquid handler system may be used in addition to, or in some examples, in lieu of, the bead mover system.

The methodology involves equilibrating a first type of magnetic beads 208 in an appropriate equilibration buffer. It may be understood that the first type of magnetic beads 208 selected for use include a first recognition element 210 capable of recognizing and binding to an affinity tag 212 coupled to the target protein 214. Between the affinity tag 212 and the target protein 214, a sequence of amino acids 216 recognizable by a protease 220 may be included.

Following equilibration, the methodology includes incubating the first type of magnetic beads 208 with the target protein 214, such that the first type of magnetic beads 208 bind, by way of the recognition element 210, the affinity tag 212. With the magnetic beads 208 bound to the target protein 214, one or more wash steps may be conducted to remove contaminating material (e.g., cellular debris, non-target proteins, nucleic acids, and the like). It may be understood that the wash steps may involve collecting the first type of magnetic beads 208 and associated target protein 214 via a magnetic rod such as that depicted in FIGS. 1A-1D, and transferring the collected magnetic beads and associated target protein to one or more different wells of microplates in a fashion that significantly reduces contaminating material.

Following the washing, the methodology involves releasing the target protein 214 from the first type of magnetic beads 208. The releasing can be accomplished by cleaving the target protein 214 from the affinity tag 212, via the protease 220 that recognizes and cleaves the particular amino acid sequence 216 between the affinity tag and the target protein 214. Next, a second type of magnetic bead 230 may be used to bind the protease 220. Specifically, the protease 220 may include a second affinity tag 222, that can be bound by a second recognition element 232. In this way, the first type of magnetic bead 208 may be bound to the affinity tag 212 (and any remaining amino acid sequence attached to the affinity tag following proteolytic cleavage), while the second type of magnetic bead 230 may be bound to the protease 220. This enables removal of all the first type and second type of magnetic beads from the solution, leaving behind purified product comprised of the target protein 214.

While the methodology of FIG. 2 is illustrated as removing all beads following proteolytic cleavage, in embodiments the first type of magnetic beads 208 may be removed following proteolytic cleavage, then the second type of magnetic beads 230 may be added, and subsequently removed. For clarity, at FIG. 2 the first type of magnetic beads 208 is also called out by bold numeral "1", and the second type of magnetic beads 230 is also called out by bold numeral "2."

Figure 3:
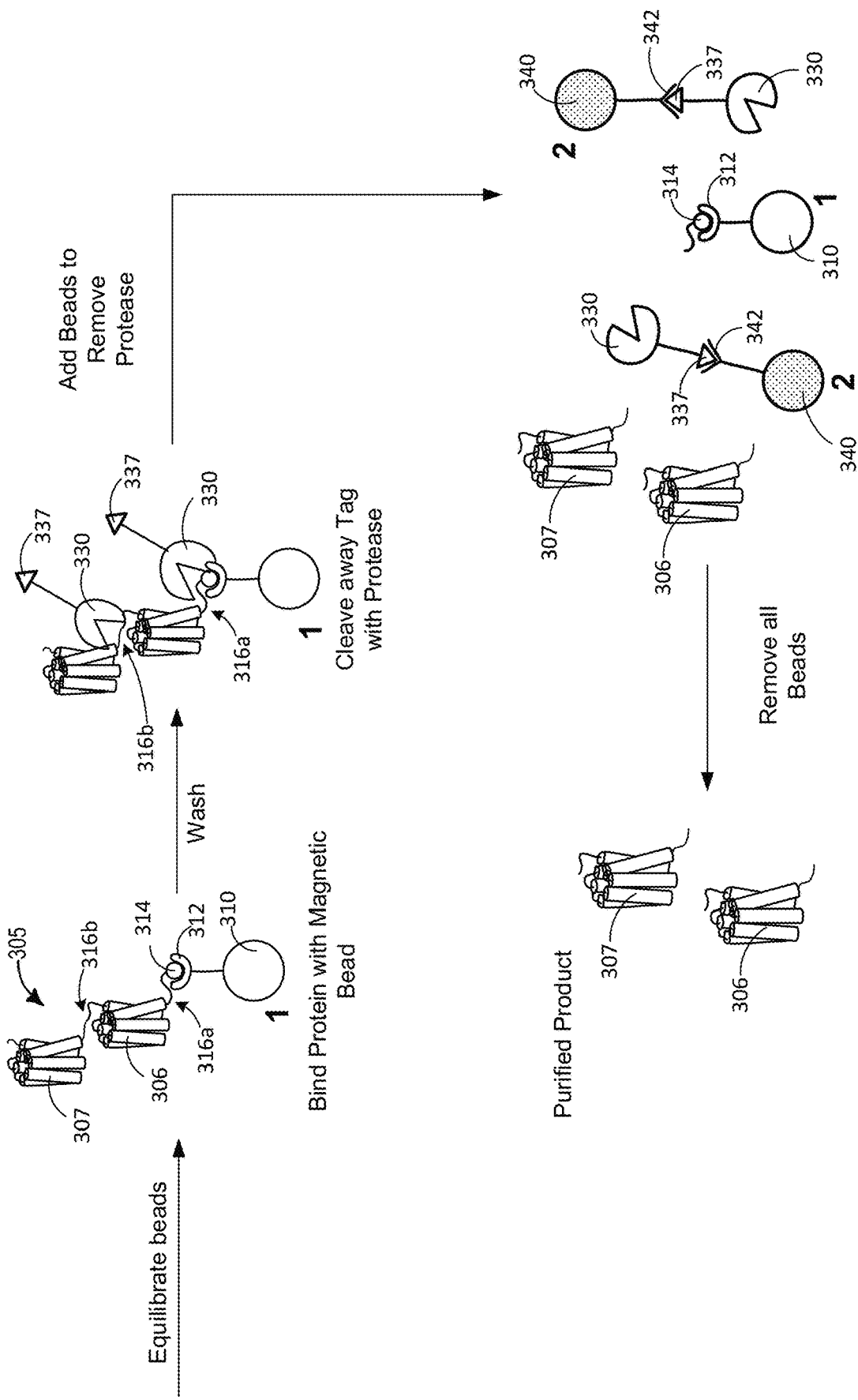
FIG. 3 illustratively depicts a method for purification of two or more target proteins, using the general methodology of that depicted at FIG. 2.

The methodology discussed with regard to FIG. 2 enables purification of a single recombinant protein that includes an affinity tag that can be proteolytically removed. Turning to FIG. 3, depicted schematically is a similar methodology that enables the purification of two or more (e.g., 3, 4, 5, or even more) proteins in similar fashion. In such methodology, the two or more proteins may be linked together as one long polypeptide chain (e.g., daisy-chained together) that also includes an affinity tag that can be cleaved away from the protein chain via proteolytic cleavage. Between each of the two or more proteins is a linker region that is also recognized by the protease capable of cleaving off the affinity tag. In this way, proteolytic cleavage with a single protease serves to both remove the affinity tag and to liberate two or more different proteins from one another, as elaborated in greater detail below.

Similar to the methodology of FIG. 2, the methodology of FIG. 3 begins with equilibration of the magnetic beads for use thereof. While not explicitly illustrated, it may be understood that, like the methodology of FIG. 2, the methodology of FIG. 3 can be conducted using an automated bead mover system (e.g., a KingFisher™ Flex). In some examples, a liquid extraction system may be used in combination with, or in lieu of, the automated bead mover system. Following equilibration of the magnetic beads, the method includes binding the recombinantly expressed polypeptide 305 with a first type of magnetic bead 310, via recognition element 312 recognizing and binding to affinity tag 314. In this example, polypeptide 305 includes first protein 306 and second protein 307. In some examples, first protein 306 and second protein 307 are different proteins, but it is also contemplated that first protein 306 and second protein 307 can be the same.

Between the affinity tag 314 and the first protein 306 is a first amino acid sequence 316a that enables proteolytic cleavage of the affinity tag 314 from polypeptide 305. There is a second amino acid sequence 316b between the first protein 306 and the second protein 307, that also enables proteolytic cleavage of the first protein 306 from the second protein 307. It may be understood that a same protease 330 (e.g., TEV protease) can cleave both the first amino acid sequence 316a and the second amino acid sequence 316b. However, it may also be understood that although the same protease can recognize and cleave both the first amino acid sequence 316a and the second amino acid sequence 316b, there may be differences between the first amino acid sequence 316a and the second amino acid sequence 316b, without departing from the scope of this disclosure. For example, each of first amino acid sequence 316a and second amino acid sequence 316b may each include the amino acid sequence that is capable of being recognized and cleaved via the protease, but in some examples there may be some differences in sequence to enable expression of both the first protein 306 and the second protein 307. For example, second amino acid sequence 316b may in some examples include a greater number of amino acids than first amino acid sequence 316a. This may act as a linker region to enable both first protein 306 and second protein 307 to properly fold even though linked in a single polypeptide chain 305. In other examples, the first amino acid sequence 316a may be of a greater length than second amino acid sequence 316b. In other examples, first amino acid sequence 316a and second amino acid sequence 316b may be of a same length, and of either a same amino acid sequence or a different amino acid sequence (but at a minimum including the sequence recognizable by the same protease).

Accordingly, following equilibration of the magnetic beads, the polypeptide 305 may be bound to the first type of magnetic bead 310. Subsequent to the binding of the first type of magnetic bead 310 to the polypeptide 305, the methodology includes conducting any number of wash steps to remove contaminating material. Following the wash steps, the methodology includes cleaving away the affinity tag 314 from the polypeptide 305, via the protease 330 recognizing and cleaving first amino acid sequence 316a. The protease 330 additionally recognizes and cleaves second amino acid sequence 316b, thereby releasing the first protein 306 from the second protein 307. It may be understood that protease 330 includes a second affinity tag 337.

Once the affinity tag 314 has been removed and the first protein 306 and second protein 307 are proteolytically released, the methodology includes adding a second type of magnetic bead 340, where the second type of magnetic bead 340 includes a second recognition element 342 that specifically recognizes and binds to the second affinity tag 337 associated with the protease 330. Hence, the first type of magnetic bead 310 remains bound to the affinity tag 314, whereas the second type of magnetic bead 340 binds to protease 330 by way of the second affinity tag 337 associated with the protease. In this way, a magnetic rod (not shown at FIG. 3 but refer to FIGS. 1A-1D) can be used to remove all of the first type of magnetic beads 310 and the second type of magnetic beads 340, but where the magnetic rod has no attraction to proteins 306 and 307. Hence, following removal of the first and second types of magnetic beads, what remains is the purified product comprised of first protein 306 and second protein 307.

While the methodology of FIG. 3 is illustrated as removing all beads following proteolytic cleavage, in embodiments the first type of magnetic bead 310 may be removed following proteolytic cleavage, then the second type of magnetic bead 340 may be added, and subsequently removed. For clarity, at FIG. 3 the first type of magnetic beads 310 is also called out by bold numeral "1", and the second type of magnetic beads 340 is also called out by bold numeral "2."

The methodology schematically illustrated in FIG. 3 may enable more than two proteins (e.g., more than two different proteins, same protein, or some combination) to be expressed and purified, provided that between each protein, a same protease cleavage site is included so that a single protease is capable of releasing the polypeptide from the single affinity tag, and also releasing each of the single proteins from one another. For example, the methodology of FIG. 3 may be used to purify three proteins, four proteins, five proteins, or in some examples more than five proteins. The methodology may be advantageous in that time required for purification of more than one protein may be reduced, as compared to separate purifications for each protein, provided that it is desired to have the two or more proteins in a same solution following the purification.

Figure 4:
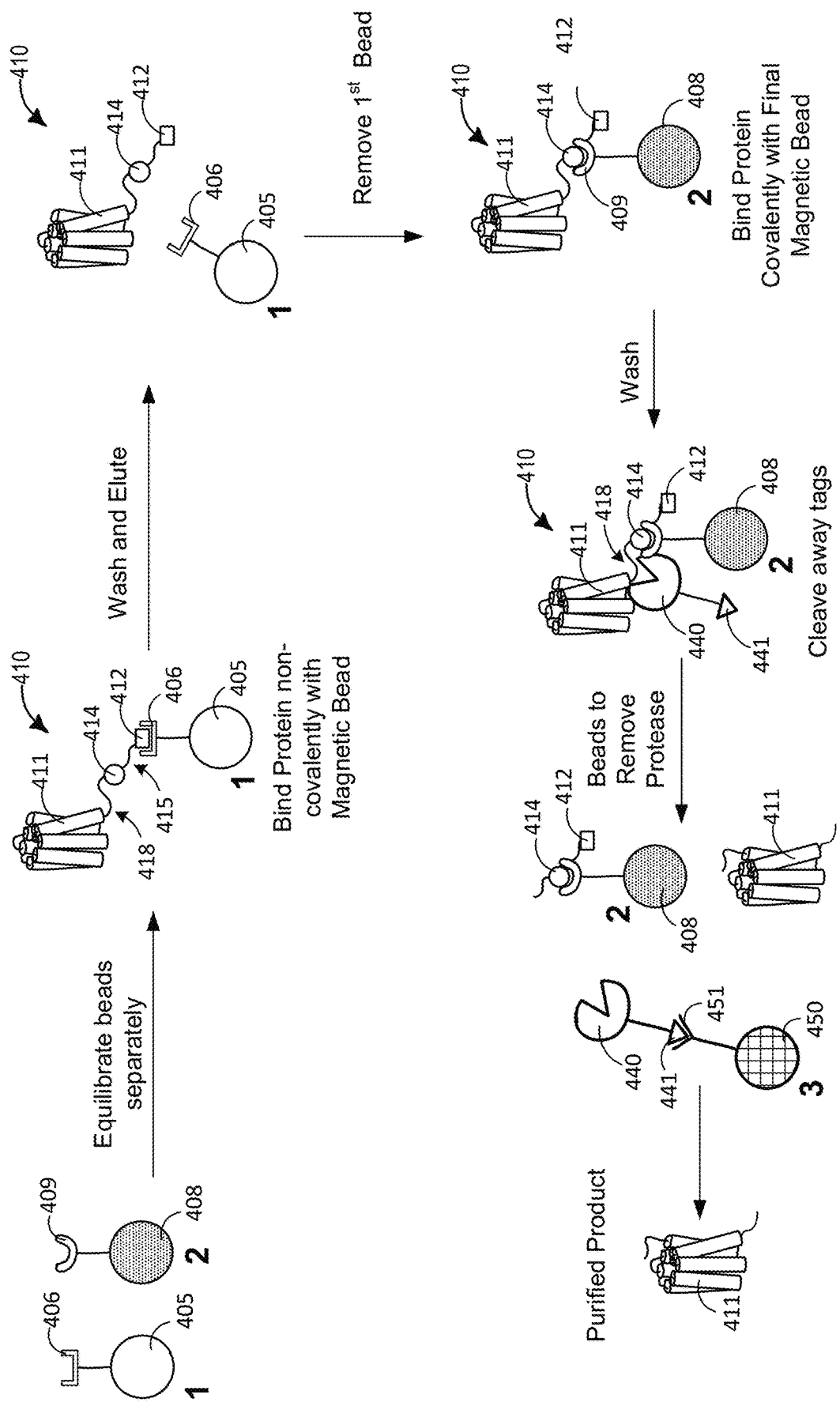
FIG. 4 illustratively depicts a method for purification of one or more target proteins with a plurality of magnetic beads, where the target protein includes a first affinity tag and a second affinity tag on a same terminus of the target protein.

Turning now to FIG. 4, depicted is another example methodology for purification of a recombinantly expressed polypeptide. In this example, the polypeptide 410 is expressed with a first affinity tag 412, and a second affinity tag 414. The first affinity tag 412 may enable non-covalent binding of the first affinity tag with a first recognition element 406 coupled to a first type of magnetic beads 405. The second affinity tag 414 may enable covalent binding of the second affinity tag with a second recognition element 409 coupled to a second type of magnetic beads 408. The polypeptide 410 may include a first linker region 415 between the first affinity tag 412 and the second affinity tag 414, and may include a second linker region 418 between the second affinity tag 414 and the target protein 411. The second linker region 418 may be comprised of an amino acid sequence that is recognized by a particular protease (e.g., TEV), while the first linker region 415 may lack the amino acid sequence such that the protease does not recognize and/or cleave the first linker region 415.

The methodology includes first separately equilibrating the magnetic beads 405 and 408 including recognition elements 406 and 409, respectively, specific to each affinity tag 412 and 414, respectively. Next, the first type of magnetic beads 405 are used to bind the polypeptide 410 by way of the first affinity tag 412. This first binding step comprises a non-covalent interaction between the first affinity tag 412 and the first recognition element 406 coupled to the first type of magnetic beads 405. As a representative example, the first affinity tag 412 may comprise a His-tag, and the first recognition element 406 may comprise a nitrillotriacetic acid (NTA) chelation moiety loaded with divalent nickel ions ($Ni^{2+}$). Following the binding, any number of wash steps may be conducted, to remove or at least significantly reduce contaminating material. Once the washes have been conducted, the methodology involves eluting the polypeptide 410 from the first type of magnetic beads 405. In the case of a His-tag, imidazole may be used to reduce the affinity of the first affinity tag 412 for the first recognition element 406. In other examples, different manners of elution may be used, depending on the nature of the affinity tag and the recognition element coupled to the magnetic bead.

Following elution of the polypeptide 410 from the first type of magnetic beads 405, the first type of magnetic beads 405 may be removed. Specifically, a magnetic rod (not shown at FIG. 4 but refer to FIGS. 1A-1D) may be lowered into a solution containing the eluted polypeptide 410 and the first type of magnetic beads 405, such that just the first type of magnetic beads 405 are attracted, and thus bind, to the magnetic rod. In this way, the first type of magnetic beads 405 may be removed from the sample containing the polypeptide 410.

Next, the polypeptide 410 may be covalently bound to the second type of magnetic beads 408 via covalent interaction between the second affinity tag 414 and the second recognition element 409 coupled to the second type of magnetic beads 408. In a representative example, the second affinity tag 414 is a HaloTag, and the second recognition element 409 is a HaloTag ligand (although other covalent tag/ligand pairings may be used without departing from the scope of this disclosure). Once covalently bound, any number of wash steps may again be conducted, to further remove any contaminating material.

Following the washing, a protease 440 (e.g., TEV) containing a third affinity tag 441 may be used to release the target protein 411 from the second type of magnetic beads 408, leaving the first affinity tag 412 and second affinity tag 414 bound to the second type of magnetic beads 408.

With the target protein 411 released from the second type of magnetic beads 408, a third type of magnetic bead 450 may be added to the sample in order to bind the protease 440. Specifically, the protease 440 may include a third affinity tag 441, and the third type of magnetic beads 450 may include a third recognition element 451, that specifically recognizes and binds to the third affinity tag 441. In this way, the third type of magnetic beads 450 may bind the protease 440, while the first affinity tag 412 and second affinity tag 414 remain bound to the second type of magnetic beads 408. While not explicitly illustrated, a magnetic rod (refer to FIGS. 1A-1D) may be used to remove each of the second type of magnetic beads 408 and the third type of magnetic beads 450, thereby resulting in the purified target protein 411. Via the use of unique tags on the protease, the possibility of reaching a binding capacity limit of the beads that may inhibit removal of the protease, may be reduced. That said, in examples, the third affinity tag 441 may be the same as the second affinity tag 414, without departing from the scope of this disclosure.

While not explicitly illustrated, the methodology of FIG. 4 may be used in similar fashion (e.g., combined with) as the methodology of FIG. 3, where more than one target protein is purified as a polypeptide of two, three, or more proteins. In other words, the methodology of FIG. 4 is not limited to purification of a single protein, but can be used to purify more than one protein in similar fashion as the methodology of FIG. 3.

For clarity of FIG. 4, the first type of magnetic beads 405 is also called out by bold numeral "1", the second type of magnetic beads 408 is also called out by bold numeral "2", and the third type of magnetic beads 450 is also called out by bold numeral "3."

Figure 5A:
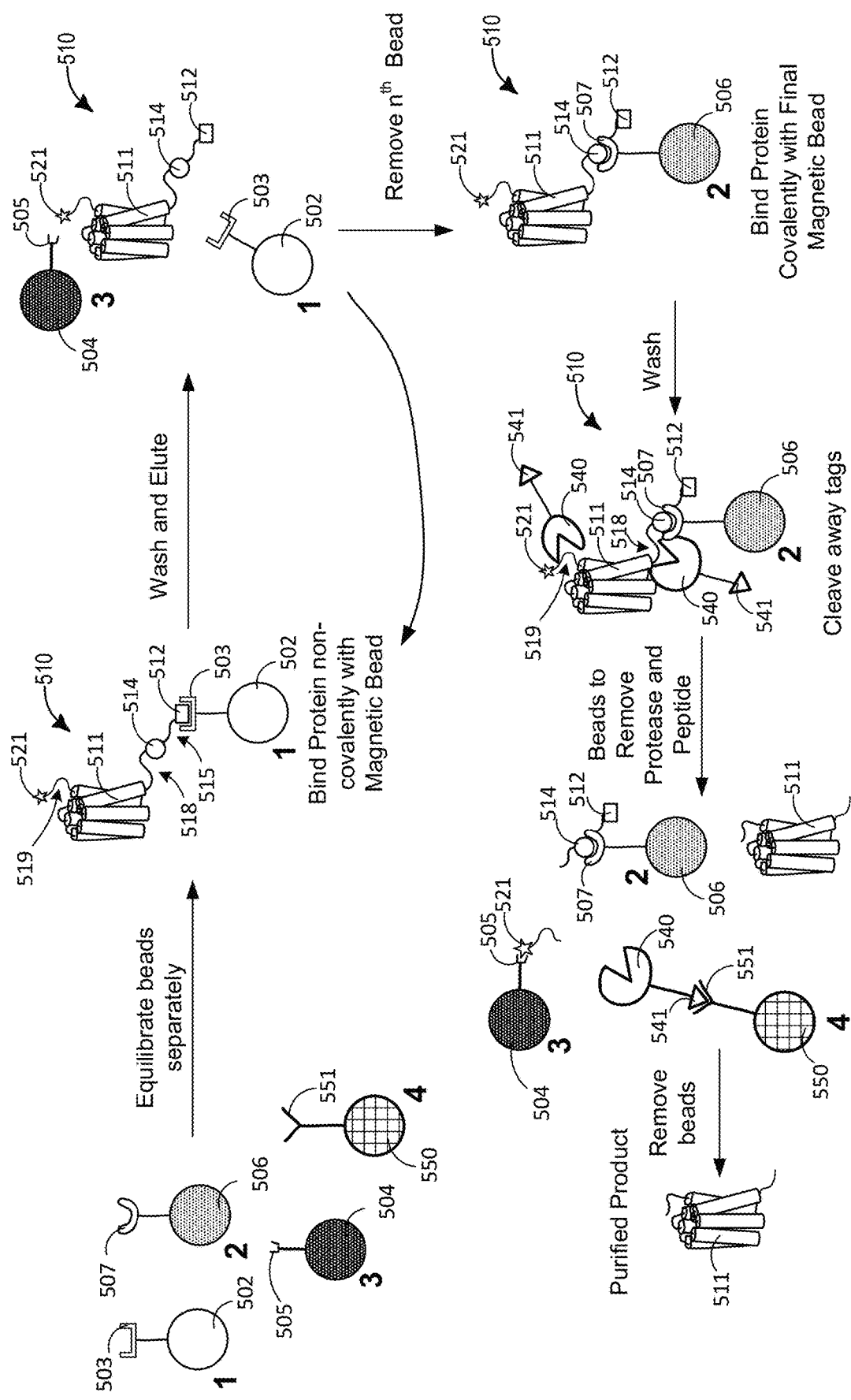
FIGS. 5A-5B illustratively depict methods for purification of one or more target proteins with a plurality of magnetic beads, where the target protein includes a first affinity tag and a second affinity tag on one terminus of the target protein, and at least a third affinity tag on the other terminus of the target protein.
Figure 5B:
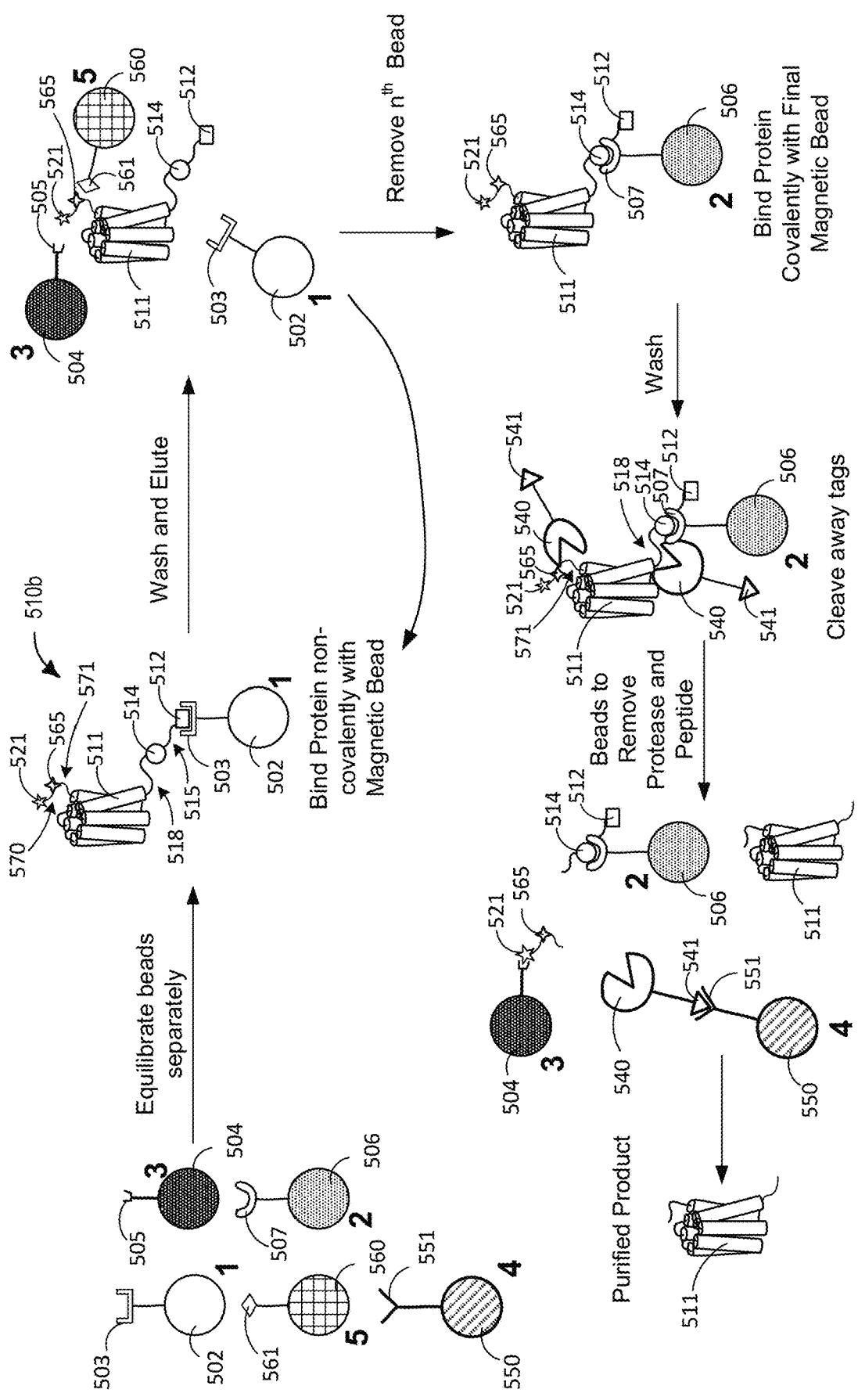

The methodology of FIG. 4 was discussed with regards to the use of a polypeptide with one affinity tag that is used to non-covalently bind magnetic beads, and another affinity tag used to covalently bind magnetic beads. In the example methodology discussed, both of the tags were on a same terminus of the protein. Variations to the methodology discussed with reference to FIG. 3 are herein contemplated. Turning to FIGS. 5A-5B, depicted is a schematic illustration of methodology to purify proteins using a multiple magnetic bead approach, with a plurality of non-covalent affinity tags and a single covalent affinity tag. In this example, the non-covalent affinity tags are included on both termini of the recombinantly expressed polypeptide, with a single covalent affinity tag included on one termini of the recombinantly expressed polypeptide.

The methodology involves use of a first type of magnetic bead 502, including a first recognition element 503; a second type of magnetic bead 506, including a second recognition element 507; a third type of magnetic bead 504, including a third recognition element 505; and a fourth type of magnetic bead 550, including a fourth recognition element 551. For clarity, the first type of magnetic bead 502 is also called out by bold numeral "1", the second type of magnetic bead 506 is also called out by bold numeral "2", the third type of magnetic bead 504 is also called out by bold numeral "3", and the fourth type of magnetic bead 550 is also called out by bold numeral "4."

For the methodology, a recombinantly expressed polypeptide 510 includes, at a first terminus, a first affinity tag 512 capable of non-covalently binding to the first type of magnetic bead 502 by way of first recognition element 503. The polypeptide additionally includes, at the first terminus, and a second affinity tag 514 capable of covalently binding to the second type of magnetic bead 506 by way of second recognition element 507. A first linker region 515 is included at the first terminus between the first affinity tag 512 and the second affinity tag 514, and a second linker region 518 is included at the first terminus between the second affinity tag 514 and the target protein 511. The second linker region 518 includes an amino acid sequence recognizable by a selected protease (e.g., TEV), but the first linker region 515 lacks this amino acid sequence. The polypeptide 510 also includes, at a second terminus, a third affinity tag 521 capable of non-covalently binding to the third magnetic bead 504 by way of the third recognition element 505. Between the target protein 511 and the third affinity tag 521 is a third linker region 519 that also includes the amino acid sequence recognizable by the selected protease.

Briefly, the methodology involves first equilibrating each of the four types of magnetic beads separately. Next, the methodology includes binding the polypeptide 510 non-covalently with the first type of magnetic bead 502. Specifically, the first type of magnetic bead 502 includes recognition element 503 which binds the polypeptide 510 via the first affinity tag 512. Once bound, the method includes proceeding through any number of wash steps, followed by elution of the polypeptide 510 from the first type of magnetic bead 502. As a representative example, the first affinity tag 512 may be a His-Tag capable of being eluted from the first type of magnetic bead 502 by imidazole.

Following elution (and in examples, removal of the first type of magnetic bead), the methodology includes binding the polypeptide 510 non-covalently with the third type of magnetic bead 504. Specifically, the third type of magnetic bead 504 may non-covalently bind the polypeptide 510 through interaction of the third recognition element 505 with the third affinity tag 521. As a representative example, the third affinity tag 521 is a Strep tag, and the third type of magnetic beads 504 may bind the Strep tag in a manner that enables elution of the polypeptide 510 from the third type of magnetic beads 504 via the use of biotin, for example. Hence, following the binding, any number of wash steps may be conducted, followed by elution of the polypeptide 510 from the third type of magnetic beads 504.

In embodiments, following each elution from the particular type of magnetic beads, the magnetic beads may be removed (e.g., via a magnetic rod as discussed).

Following the elution from the $n^{th}$ magnetic bead (two in this example), the methodology includes binding the polypeptide 510 covalently to the second type of magnetic beads 506. Specifically, the second type of magnetic beads 506 may bind the polypeptide 510 via the second recognition element 507 recognizing and binding to the second affinity tag 514. In a representative example, the second recognition element 507 may be a HaloTag ligand, and the second affinity tag 514 may be a HaloTag.

Following the covalent binding, the methodology includes conducting any number of wash steps to reduce/remove contaminating material. Next, the methodology involves releasing the target protein 511 from the second type of magnetic beads 506, via the use of protease 540. Protease 540 cleaves the amino acid sequence comprising the second linker region 518 and the third linker region 519, but does not cleave the first linker region 515. In this way, both the first affinity tag 512 and second affinity tag 514 remain bound to the second type of magnetic bead 506. The cleavage of the third linker region 519 releases the target protein 511 from the third affinity tag 505. Accordingly, the next step involves binding the protease 540 with the fourth type of magnetic bead 550, via interaction of the fourth recognition element 551 with the fourth affinity tag 541 included as part of protease 540. Additionally, the third type of magnetic beads 504 is used to bind the third affinity tag 521, following its cleavage from polypeptide 510. Following the binding of the protease 540 to the fourth type of magnetic beads 550, and the binding of the third affinity tag 521 to the third type of magnetic beads 504, removal of all remaining magnetic beads (e.g., via a magnetic rod as discussed with regard to FIGS. 1A-1D) yields the purified product comprising the target protein 511.

FIG. 5B depicts another example of the same methodology of FIG. 5A, with an additional non-covalent affinity tag, specifically fourth affinity tag 565. Because the methodology of FIG. 5B is substantially similar to that of FIG. 5B, same numerals are used, except where explicitly noted. The inclusion of the fourth affinity tag 565 renders the polypeptide slightly different than that of FIG. 5A, hence the polypeptide is numbered as polypeptide 510b. The polypeptide 510b includes the first linker region 515 and second linker region 518, similar to FIG. 5A. Additionally, the polypeptide 510b includes third linker region 571, and fourth linker region 570. Third linker region 571 is positioned between the target protein 511 and the third affinity tag 565, while the fourth linker region 570 is positioned between the third affinity tag 565 and the fourth affinity tag 521. The second linker region 518 and the third linker region 571 each include an amino acid sequence capable of being recognized and cleaved via the protease 540, however the first linker region 515 and fourth linker region 570 lack this amino acid sequence.

As mentioned, the methodology of FIG. 5B is the same as that of FIG. 5A, but specifically illustrates the use of one more non-covalent affinity tag, specifically fourth affinity tag 565. As a representative example, the fourth affinity tag 565 may be maltose-binding protein, which may, for example, enable elution from a fifth type of magnetic bead 560 (including fifth recognition element 561) via the use of amylose.

Accordingly, the methodology of FIG. 5B includes binding and eluting the polypeptide 510b three times, prior to covalently binding the polypeptide 510b to the second type of magnetic beads 506. Specifically, the methodology includes first non-covalently binding the polypeptide 510b to the first type of magnetic beads 502, followed by washing and elution of the polypeptide 510b. Next, the methodology includes non-covalently binding the polypeptide 510b to the third type of magnetic beads 504, followed by washing and elution of the polypeptide 510b. Next, the methodology includes non-covalently binding the polypeptide 510b to the fifth type of magnetic beads 560, followed by washing and elution of the polypeptide 510b. It may be understood that the first non-covalent binding is via the first recognition element 503 binding the first affinity tag 512, the second non-covalent binding is via the third recognition element 505 binding the third affinity tag 521, and the third non-covalent binding is via the fifth recognition element 561 binding the fourth affinity tag 565. In embodiments, after each elution step, the magnetic beads used for that particular step may be removed (e.g., via a magnetic rod).

Once all of the non-covalent binding, washing, and eluting steps have been conducted, the methodology includes covalently binding the polypeptide 510b with the second type of magnetic bead 506. Following washing steps, the protease 540 is used to cleave the polypeptide 510b at the second linker region 518 and the third linker region 571. Accordingly, the target protein 511 is released from the second type of magnetic beads 506, with the first affinity tag 512 and second affinity tag 514 remaining bound to the second type of magnetic beads. Additionally the target protein 511 is released from the third affinity tag 521 and the fourth affinity tag 565. Accordingly, in a next step, the fourth type of magnetic beads 550 is used to bind the protease 540, via interaction between the fourth recognition element 551 and the affinity tag 541 associated with the protease 540. Additionally, the third type of magnetic beads 504 is used to bind the third affinity tag 521 (or alternatively, the fifth type of magnetic beads 560 is used to bind the fourth affinity tag 565. Following the binding, all of the magnetic beads remaining may be removed via a magnetic rod (see FIGS. 1A-1D), resulting in the purified product comprising the target protein 511.

While this example of FIG. 5B illustrates the use of four affinity tags (three of which are used for non-covalent interaction with magnetic beads, and one of which is used for covalent interaction with other magnetic beads), it may be understood that it is within the scope of this disclosure that even more affinity tags can in principle be used (e.g. four non-covalent affinity tags, five non-covalent affinity tags, etc.). Similar to that discussed above with regard to FIG. 5A, using a unique affinity tag for the protease may be advantageous in that the possibility of reaching a binding capacity limit of beads used to remove the protease may be reduced (although it is within the scope of this disclosure that a same type of magnetic bead used to bind the released peptide comprising one or more affinity tags (e.g., affinity tags 521 and 565 at FIG. 5B) may be used to bind the protease in some examples where the protease includes the appropriate affinity tag (e.g., either affinity tag 521 or 565).

Thus, as discussed herein, the use of magnetic bead technology as herein disclosed relies on at least one affinity tag fused to the protein of interest. The at least one affinity tag is removable through the use of a protease (e.g., TEV protease), via inclusion of a specific target sequence between the protein of interest and the tag that is recognized and cleaved via the protease. It is contemplated that any sequence specific protease can be used, including commercially available sequence specific proteases (e.g., New England Biolabs® Inc.). After cleavage, the tag remains bound to the bead, but the protein of interest is released to the supernatant. However, the protein of interest is also accompanied by the protease in the supernatant as well. This requires that the protease be removed from the supernatant to obtain purified protein of interest. Some protocols for protein purification recommend the use of a protease fused to the same tag as the protein of interest. The reason for that is to achieve simultaneous cleavage and removal from the supernatant. One potential issue there is that if the beads are already saturated with bound protein tag, then the protease may not be removed efficiently, hence the advantage of using a unique affinity tag for the protease in the methodology herein disclosed.

There are protocols for protein purification which exist that make use of agarose beads for protein purification. In such protocols, it is implied that silica beads specific to the removal of the protease be used, but this is not amenable to automation. In the methodology herein disclosed, magnetic beads specific to the removal of protease are used to accommodate automation and maximize removal of the protease. Another advantage realized via the disclosed methods is in the avoidance altogether of detergents. Specifically, in a representative example, the methodology herein disclosed enables avoidance of IGEPAL CA-630 from purification buffers, which is required while using the agarose beads. The use of IGEPAL CA-630 ensures that agarose beads are prevented from sticking to laboratory plastics, which would otherwise result in loss of beads, and hence, sample. In contrast, it is herein recognized that magnetic beads for use with the methodology herein disclosed have no issues with sticking to lab plastics (e.g., micro- or deep well plates).

The use of IGEPAL CA-630 is problematic because it interferes with most all protein quantification methods (e.g. Qubit, Pierce 660). IGEPAL is a detergent and absorbs at a wavelengths of ~230 nm and ~280 nm in similar fashion to RIPA buffer absorbance interference. This is because nonident P-40 found in RIPA buffer is chemically substantially identical to IGEPAL CA-630. This wavelength interference prevents direct quantitation of proteins using spectroscopy. Because IGEPAL CA-630 is a detergent, it interferes with Qubit measurements as well due to hydrophobic binding of the fluorescent signal molecules, and many other protein quantitation methods such as Pierce 660, Bradford, and Lowry. The interference of protein quantitation by including IGEPAL CA-630 in purification buffer severely limits which methods can be used to quantify, and restricts us to methods that have high sample-to-sample variability.

The disclosed method which uses dual magnetic beads has numerous advantages including IGEPAL CA-630 not being needed in purification buffers because magnetic beads do not stick to lab plastic, and this allows for easy and accurate downstream quantification of purified protein product. Another improvement is that the entire purification protocol from bead equilibration to purified protein product can be completed on an automated extraction system, such as the KingFisher™ Flex, without any centrifuging steps and which in turn minimizes human interaction during the purification. The use of automated protein purification allows numerous samples to be processed at once, such as 1 to 96 samples in a short amount of time. For example, using the methodology of FIGS. 2-3, 1 to 96 samples may be processed (e.g., purified) in four hours or less. It may be understood that the inclusion of additional affinity tags in the recombinantly expressed protein (see examples of FIGS. 4-5B) may result in purification times that are at least somewhat longer, due to the additional washing and elution steps associated with the purification schemes. However, in some examples any disadvantage of additional time may be offset by the greater purity of final product, and even where the time to purify may be somewhat higher, the overall time for purification of a number of proteins may still be substantially lower than if the proteins were attempted to be purified by more manual methodology.

It is contemplated that the disclosed methods and systems may be advantageous for protein purification in any laboratory setting, including academic labs interested in protein purification and/or for high-throughput commercial laboratories. It is contemplated that the disclosed methods and systems result in proteins of at least 80% purity, such as at least 85%, at least 90%, at least 95% purity, including between about 80% to 90% purity, 90% to 100% purity, including 80%, 81%, 82%, 83%, 84%, 85%, 86%, 87%, 88%, 89%, 90%, 91%, 92%, 93%, 94%, 95%, 96%, 97%, 98%, 99% or 100% purity.

As mentioned above, the use of automated protein purification as herein disclosed enables numerous samples to be processed at once, such as 1-96 samples. Taking as an example 96 samples, in one embodiment the disclosed methodology enables purification of 96 proteins (e.g., 96 different proteins), provided that each well includes a polypeptide that corresponds to a single target protein (refer to the methodology of FIG. 2). However, it may be understood that in another example comprising the processing of 96 samples, particular wells can include a polypeptide that comprises more than one target protein (refer to the methodology of FIG. 3). Hence, in embodiments, the processing of 96 samples (as an example) may yield a number of purified target proteins greater than 96. As a representative example where each well includes a polypeptide corresponding to two target proteins, then processing of the 96 samples can yield 192 target proteins. As another representative example where each well includes a polypeptide corresponding to three target proteins, then processing of the 96 samples can yield 288 target proteins. Any number of iterations are within the scope of this disclosure. For example, a number of wells can include polypeptides corresponding to one target protein, while other wells can include polypeptides corresponding to more than one target protein (e.g., 2, 3, 4, or even 5 or more).

The various methodologies detailed above were discussed in the context of reliance on cell lysates to enable magnetic beads with corresponding recognition elements to bind to target proteins by way of affinity tags. It is also within the scope of this disclosure that the polypeptide that ultimately yields the target protein, in embodiments, can include a secretion signal peptide, for secretion from the host cell to the surrounding environment. In general, secretion signal peptides are located at the N-terminus of proteins and their length ranges from about 15-30 amino acids, but it is within the scope of this disclosure that in some examples the secretion signal peptide can be included at the C-terminus. In examples, the secretion signal peptide may be at an opposite terminus of the polypeptide as compared to the covalent affinity tag (e.g., HaloTag, SNAP tag). In examples, the secretion signal peptide may be at a same terminus of the polypeptide as compared to the covalent affinity tag. In examples, release of the target protein via proteolytic cleavage from the polypeptide which is covalently bound to a magnetic bead may additionally release the target protein from the signal secretion peptide (e.g., the protease cleaves away both the secretion signal peptide and at least the covalent affinity tag). In other examples, the target protein may be released from the polypeptide via proteolytic cleavage without also cleaving away the secretion signal peptide (e.g., the protease cleaves off the covalent affinity tag without also cleaving off the signal secretion peptide). Addition of a secretion signal peptide may enable the methodologies of FIGS. 2-5B to be conducted, in some examples, in lieu of (or in some examples in addition to) a cell lysis step, given that the polypeptide comprising the target protein is secreted from the host cells. Choice of signal secretion peptide in such examples is host dependent and can be selected based on desired expression/secretion profiles.

It is additionally herein recognized that, in examples, the covalent tag (e.g., HaloTag) can be used as a fluorescent protein when coupled to particular ligands. There are a number of ligands that may be used which enable fluorescence detection of an expressed protein harboring a covalent tag (e.g., HaloTag) responsive to the ligand being bound to the expressed protein by way of the HaloTag. Examples of cell-impermeant ligands include but are not limited to HaloTag® Alexa Fluor® 488 ligand, and HaloTag® Alexa Fluor® 600 ligand. Examples of cell-permeant ligands include but are not limited to HaloTag® TMR ligand, HaloTag® Oregon Green® ligand, HaloTag® diAcFAM ligand, HaloTag® coumarin ligand, HaloTag® TMRDirect™ ligand, and HaloTag® R110Direct™ ligand. In one embodiment, fluorescent detection of ligand interaction with the covalent tag (e.g., HaloTag) may be used to detect and, in examples, quantify, secretion of recombinantly expressed proteins to the environment. Fluorescence may be detected, for example, via a fluorometer such as a Qubit fluorometer (Thermo-Fisher Scientific, Waltham, MA), or other similar plate reader. Quantification may be conducted by comparison of fluorescence intensity of expressed proteins to a standard curve. In other examples, similar methodology can be used to quantify protein expression in cells, for example in combination with a technology such as fluorescence-activated cell sorting (FACS).

Also within the scope of this disclosure is purification of protein complexes, by way of a variation of the methodology of FIG. 3. As discussed above with respect to FIG. 3, purification of two or more target proteins at once can be accomplished by including the different proteins as a single polypeptide that includes protease sites between the target proteins as well as between the target proteins and the covalent tag. In this way, when the protease cleave away the covalent affinity tag, thereby releasing the target proteins from the affinity tag and in turn, the particular magnetic bead, the protease additionally cleaves the target proteins from one another. In such an example, the same protease cleaves the target proteins from the affinity tag and from each other. However, in other embodiments, the protease cleavage site between target proteins can be different than that of the protease cleavage site between the target proteins and the covalent affinity tag. In such an example, the host cell may recombinantly express the protease that cleaves the target proteins from one another, but may not express another protease that specifically cleaves the target proteins from a single covalent affinity tag. The target proteins cleaved in the context of the cell by way of the expressed protease may form a complex with the protein that remains coupled to the covalent affinity tag. Then, the covalent affinity tag may be used to bind to a magnetic bead via an appropriate recognition element, as discussed. Purification conditions can be selected to avoid, if possible, dissociation of the complex of proteins (e.g., gentle extraction and purification conditions). If the binding of proteins that form the complex is strong enough, then the entire complex may be purified following the cleavage of the affinity tag from the corresponding target protein.

Figure 6:
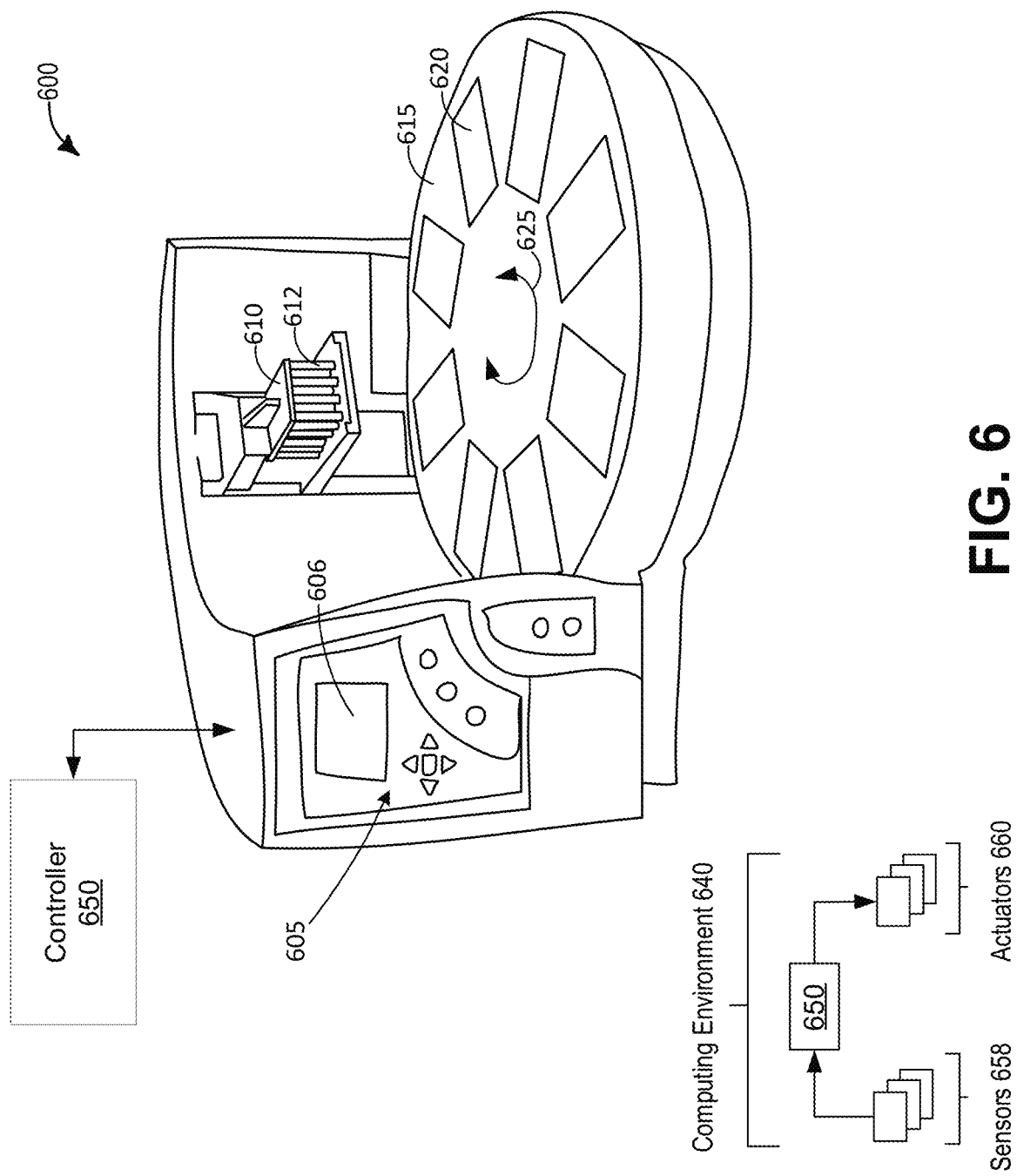
FIG. 6 depicts an automated magnetic bead mover system in accordance with embodiments of the present disclosure.

Turning now to FIG. 6, depicted is an exemplary automated bead mover system 600 (e.g., KingFisher™ Flex system), for use with embodiments disclosed herein. The automated bead mover system 600 is depicted at a high level for illustrative purposes. Bead mover system 600 may include at least a human machine interface (HMI) 605, including display 606. Via the HMI, a user may select pre-programmed programs for purification of biomolecules (e.g., DNA, protein, etc.), or may use the HMI to create user-defined programs. Automated bead mover system 600 may also include magnet head 610 which comprises a plurality of magnetic rods 612. The magnetic rods 612 may be used to collect magnetic beads and may further be used to transfer collected magnetic beads to one or more different plates (not shown). As discussed with regard to FIGS. 1A-1D, magnetic rods 612 may be slidingly coupled to disposable tips (not shown at FIG. 6), so that relative movement of the magnetic rods 612 with respect to the tips enables the collecting and releasing of magnetic beads used in the methodology disclosed herein.

Automated bead mover system 600 may additionally include turntable 615, and individual plate stations 620. Turntable 615 may move in one or more directions, exemplified by double-sided arrow 625, so as to move particular individual plate stations to preselected locations.

While HMI 605 may be used in some examples to program any number of operational aspects of bead mover system 600, in examples bead mover system 600 may be communicably coupled to a computing environment 640. In some embodiments, computing environment 640 may comprise HMI 605. In other words, bead mover system 600 may be part of computing environment 640, which is an interconnection of components forming a system configuration that provides a desired process response. In embodiments, the computing environment 640 comprises a controller 650 that provides logic and control instructions for the process, one or more sensors 658 that measure various physical properties, and one or more actuators 660 that change the state of the environment. The computing environment 640 may also include signaling means (not shown) that converts measurements from the sensor(s) 658 and/or instructions generated by the controller 650 into one or more signals that are then sent to other elements/components of the bead mover system 600. For example, the controller 650 may receive input data from one or more sensors 658, process the input data, and trigger the actuators 660 in response to the processed input data based on instructions or code programmed therein corresponding to one or more routines, procedures, functions, methods, etc. The computing environment 640 may operate according to an open-loop system, closed-loop system, sequence control system, and/or a batch control system.

In embodiments, the disclosed methodology relying on a two or more magnetic beads for purification of one or more target proteins may be conducted in an automated liquid handling system, rather than, or in addition to, an automated bead mover system. For example, aspects of an automated bead mover system may be combined with aspects of a liquid handler system, such that the resultant system is a combination of automated bead mover system and liquid handling system. Accordingly, turning now to FIG. 7, depicted is an exemplary liquid handling system 700, for use with the methodology disclosed herein. Briefly, an exemplary liquid handling system such as the liquid handling system 700 may be comprised of a platform 702, a frame 704, a controller 750, a HMI 705, a liquid handler 710, a drive system 720, and a pipetting module 725. Pipetting module 725 may include a plurality (e.g., 4, 8, 12, etc.) of pipettors 726. A container 730 is disposed on the platform 702. The container 730 may comprise, for example, a microwell or deep-well plate or rack containing any number of vials. The container 730 may be located in a container/rack holder 735. While not explicitly illustrated, liquid handling system 700 may include any number of containers 730 and/or container holders 735. The drive system 720 may enable the pipetting module 725 to move in three dimensions, as exemplified by coordinate system 736. For example, the pipetting module 725 may move back and forth, up and down, and front to back. While not explicitly illustrated, the drive system 720 may include one or more motors and/or gears to enable movement of the pipetting module 725 under control of controller 750.

The liquid handler 710 may be any suitable apparatus that can aspirate and/or dispense a desired amount of a liquid from or into a container. The liquid handler 710 may include, for example, a syringe or pump fluidly connected to the pipetting module 720 by one or more lengths of tubing 742. The liquid handler may also be under control of controller 750.

Similar to that discussed above with regard to FIG. 6, HMI 705 may enable a user to select particular programs for purification of protein according to methodology discussed herein. In examples, liquid handling system 700 may be communicably coupled to a computing environment 740. In some embodiments, computing environment 740 may comprise HMI 705. In other words, the liquid handling system 700 may be part of computing environment 740, which is an interconnection of components forming a system configuration that provides a desired process response. In embodiments, the computing environment 740 comprises a controller 750 that provides logic and control instructions for the process, one or more sensors 758 that measure various physical properties, and one or more actuators 760 that change the state of the environment. The computing environment 740 may also include signaling means (not shown) that converts measurements from the sensor(s) 758 and/or instructions generated by the controller 750 into one or more signals that are then sent to other elements/components of the liquid handling system 700. For example, the controller 750 may receive input data from one or more sensors 758, process the input data, and trigger the actuators 760 in response to the processed input data based on instructions or code programmed therein corresponding to one or more routines, procedures, functions, methods, etc. The computing environment 740 may operate according to an open-loop system, closed-loop system, sequence control system, and/or a batch control system.

In an embodiment, the methodology of any one of FIGS. 2-5B may be conducted in conjunction with a liquid handling system (e.g., liquid handling system 700 at FIG. 7) by, rather than moving beads from one well/plate to another well/plate, moving liquid from well/plate to other wells/plates and/or removing liquid and replacing liquid in same wells/plates. For example, wash steps may be conducted by removing liquid and then adding fresh liquid to conduct the washes. Similar logic applies to elution steps. For example, liquid may be removed from a well or wells containing magnetic beads coupled/bound to target protein, and then another liquid may be added with a compound (e.g., imidazole in the case of a His-tagged protein) that results in elution of the target protein from magnetic beads. Similar logic applies to addition of protease to release covalently bound target protein from magnetic beads. For example, liquid may be removed from magnetic beads bound to target protein, and then fresh liquid containing protease may be added so as to release the target protein from being bound to the magnetic beads. Similar logic applies to any clean-up steps. For example, following a protease cleavage step, a type of magnetic bead that binds an affinity tag included as part of the protease may be added to bind the protease, and then the liquid handling system may be programmed to remove the liquid containing the purified protein. Those of ordinary skill in the art may program such a liquid handling system in order to carry out the methodology herein disclosed.

It is also within the scope of this disclosure that various aspects of bead mover system 600 and liquid handling system 700 be combined, for example in a system that includes both bead handling and liquid handling operational capacity. As a representative example, a system such as that of the NIMBUS Presto (Hamilton Company, Reno, NV) which combines the Microlab® NIMBUS® (Hamilton Company, Reno, NV) for automated liquid handling with an integrated Thermo Scientific™ KingFisher Presto (Thermo Fisher Scientific, Inc., Waltham, Mass.) incorporating KingFisher technology is within the scope of this disclosure. Such an example is meant to be representative and non-limiting. Other systems that combine a bead mover system and a liquid handling system such that bead moving functionality along with liquid handling functionality are co-integrated, are within the scope of this disclosure.

Figure 8:
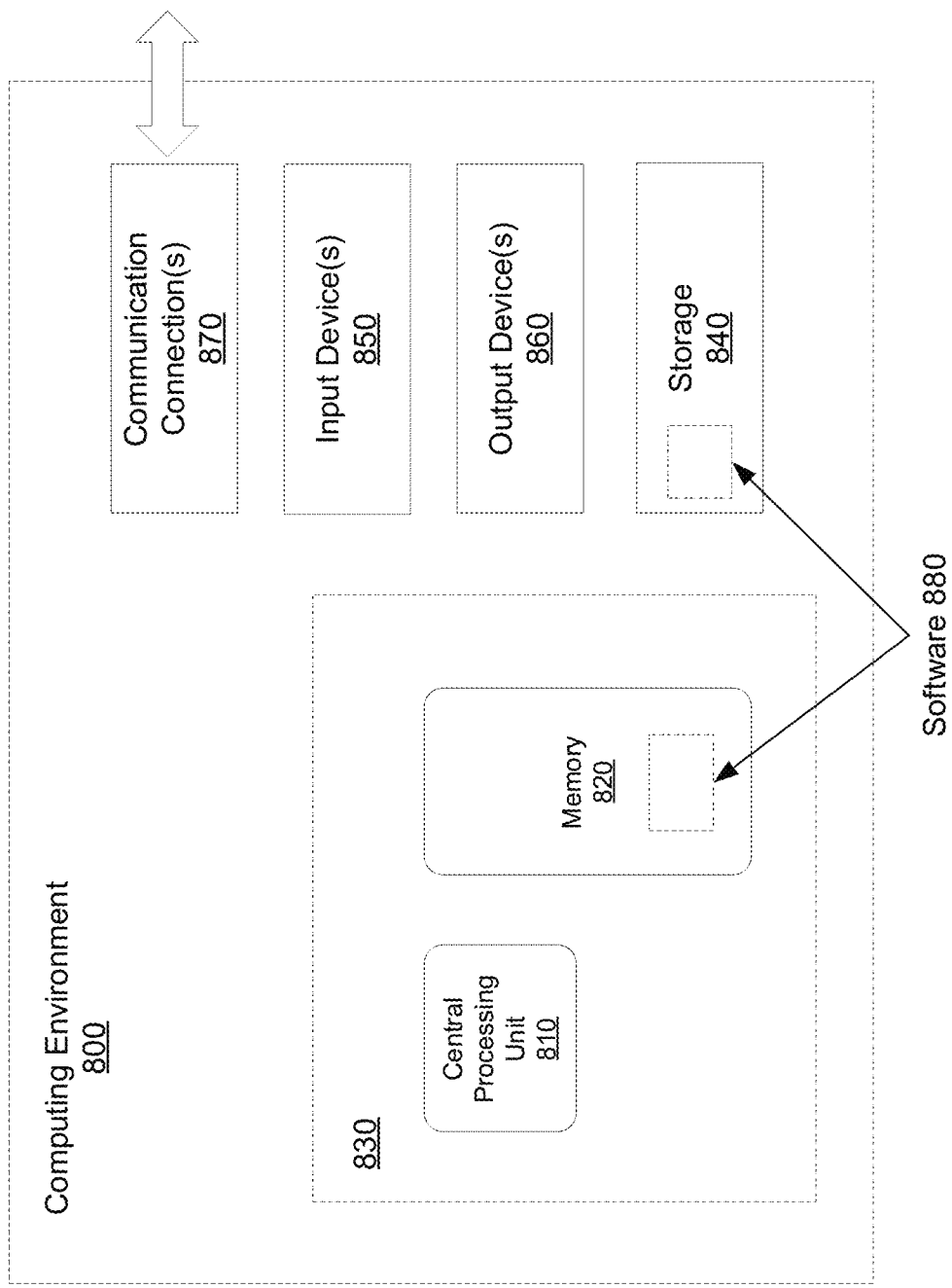
FIG. 8 depicts an example computing environment in accordance with embodiments of the present disclosure.

FIG. 8 illustrates an exemplary computing environment 800 for implementation of various aspects of the methods disclosed herein, including methodology for purification of one or more target proteins using automated purification with a plurality of different types of magnetic beads. In some embodiments, the computing environment 800 is substantially similar to or the same as computing environment 640. In some embodiments, the computing environment 800 is substantially similar to or the same as computing environment 740. Computing environment 800 may be applied to systems that combine various aspects of bead mover system 600 and liquid handling system 700. The computing environment 800 is not intended to suggest any limitation as to scope of use or functionality, as the technologies may be implemented in diverse general-purpose or special-purpose computing environments. For example, the disclosed technology may be implemented using a computing device comprising a processing unit, memory, and storage, storing computer-executable instructions implementing methods disclosed herein. The disclosed technology may also be implemented with other computer system configurations, including hand held devices, multiprocessor systems, microprocessor-based or programmable consumer electronics, network PCs, minicomputers, mainframe computers, a collection of client/server systems, and the like. The disclosed technology may also be practiced in distributed computing environments where tasks are performed by remote processing devices that are linked through a communications network. In a distributed computing environment, program modules may be located in both local and remote memory storage devices.

With reference to FIG. 8, the computing environment 800 includes at least one processing unit 810 coupled to memory 820. In FIG. 8, this basic configuration 830 is included within a dashed line. The processing unit 810 executes computer-executable instructions and may be a real or a virtual processor. In a multi-processing system, multiple processing units execute computer-executable instructions to increase processing power. The memory 820 may be volatile memory (e.g., registers, cache, RAM), non-volatile memory (e.g., ROM, EEPROM, flash memory, etc.), or some combination of the two. The memory 820 can store software 880 implementing any of the methodologies described herein.

A computing environment of the present disclosure may have additional features. For example, the computing environment 800 includes storage 840, one or more input devices 850, one or more output devices 860, and one or more communication connections 870. An interconnection mechanism (not shown) such as a bus, controller, or network interconnects the components of the computing environment 800. Typically, operating system software (not shown) provides an operating environment for other software executing in the computing environment 800, and coordinates activities of the components of the computing environment 800.

The storage 840 may be removable or non-removable, and includes magnetic disks, magnetic tapes or cassettes, CD-ROMs, CD-RWs, DVDs, or any other computer-readable media which can be used to store information and which can be accessed within the computing environment 800. The storage 840 can store software 880 containing instructions for any of the technologies described herein.

The input device(s) 850 may be a touch input device such as a keyboard, mouse, pen, or trackball, a voice input device, a scanning device, one or more sensors, or another device that provides input to the computing environment 800. For audio, the input device(s) 850 may be a sound card or similar device that accepts audio input in analog or digital form, or a CD-ROM reader that provides audio samples to the computing environment. The output device(s) 860 may be a display, printer, speaker, CD-writer, or another device such as one or more actuators that provides output from the computing environment 800.

In one example, computing environment 800 may be substantially similar to or the same as computing environment 640. In such an example, input devices 850 may comprise sensors 658, and output devices 860 may comprise actuators 660. In another example, computing environment 800 may be substantially similar to or the same as computing environment 740. In such an example, input devices 850 may comprise sensors 758, and output devices 860 may comprise actuators 760.

The communication connection(s) 870 enable communication over a communication mechanism to another computing entity. The communication mechanism conveys information such as computer-executable instructions, audio/video or other information, or other data. By way of example, and not limitation, communication mechanisms include wired or wireless techniques implemented with an electrical, optical, RF, infrared, acoustic, or other carrier.

The techniques herein can be described in the general context of computer-executable instructions, such as those included in program modules, being executed in a computing environment on a real or virtual processor. Generally, program modules include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed within a local or distributed computing environment.

Any of the disclosed methods can be implemented as computer-executable instructions or a computer program product stored on one or more computer-readable storage media (e.g., non-transitory computer-readable media, such as one or more optical media discs such as DVD or CD, volatile memory components (such as DRAM or SRAM, or non-volatile memory components such as hard drives) and executed on a computer (e.g., any commercially available computer, including smart phones or other mobile devices that include computing hardware). Computer-readable media does not include propagated signals. Any of the computer-executable instructions for implementing the disclosed methods as well as any data created and used during implementation of the disclosed embodiments can be stored on one or more computer-readable media (e.g., non-transitory computer-readable media).

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium can even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the internet, a wide-area network, a local-area network, a client-server network (such as a cloud computing network), or other such network using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, Python or any other suitable programming language. Likewise, the disclosed technology is not limited to any particular computer or type of hardware.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In embodiments, any of the software-based embodiments (including, for example, computer-executable instructions for causing a computer to perform any of the disclosed methods) can be uploaded, downloaded or remotely accessed through a suitable communication means. Such suitable communication means include, for example, the internet, the World Wide Web, an intranet, cable (including fiber optic cable), magnetic communications, electromagnetic communications (including RF, microwave, and infrared communications), electronic communications, or other such communication means.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects of a disclosed method using a computing device, in accordance with embodiments of the present disclosure. The storage medium may represent a broad range of persistent storage medium known in the art, including but not limited to flash memory, optical disks or magnetic disks. The programming instructions, in particular, may enable an apparatus, in response to their execution by the apparatus, to perform various operations described herein. For example, the storage medium may include programming instructions configured to cause an apparatus to practice some or all aspects of a disclosed method, such as a method of purifying a target protein using two or more magnetic beads, in accordance with embodiments of the present disclosure.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

Furthermore, although various example methods, apparatus, systems, and articles of manufacture have been described herein, the scope of coverage of the present disclosure is not limited thereto. On the contrary, the present disclosure covers all methods, apparatus, and articles of manufacture fairly falling within the scope of the appended claims either literally or under the doctrine of equivalents. For example, although the above discloses example systems including, among other components, software or firmware executed on hardware, it should be noted that such systems are merely illustrative and should not be considered as limiting. In particular, it is contemplated that any or all of the disclosed hardware, software, and/or firmware components can be embodied exclusively in hardware, exclusively in software, exclusively in firmware or in some combination of hardware, software, and/or firmware.

The following examples are provided to illustrate particular features of certain embodiments. However, the particular features described below should not be construed as limitations on the scope of the disclosure, but rather as examples from which equivalents will be recognized by those of ordinary skill in the art.

EXAMPLES

The following examples are put forth so as to provide those of ordinary skill in the art with a complete disclosure and description of how to make and use the methods and systems of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless otherwise indicated, parts are parts by weight, molecular weight is average molecular weight, temperature is in degrees Centigrade, and pressure is at or near atmospheric.

Example 1. Purification of Proteins by Hand Using Agarose Beads

This example demonstrates that protein purification by hand is a time-consuming an inefficient process.

Figure 9A:
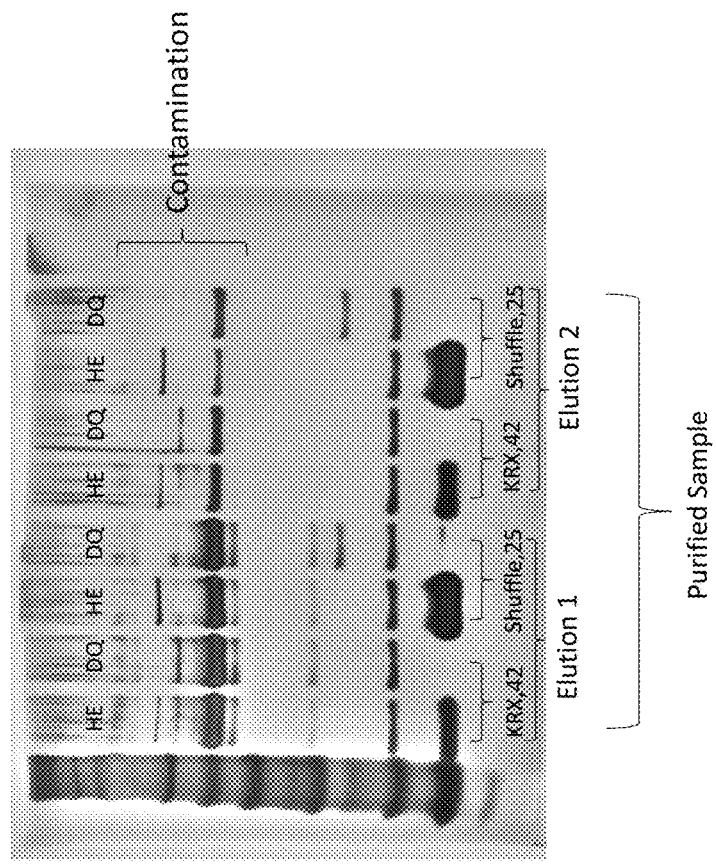
FIG. 9A is a digital image of a protein gel showing total lysate and soluble fractions of starting samples for purification.
Figure 9B:
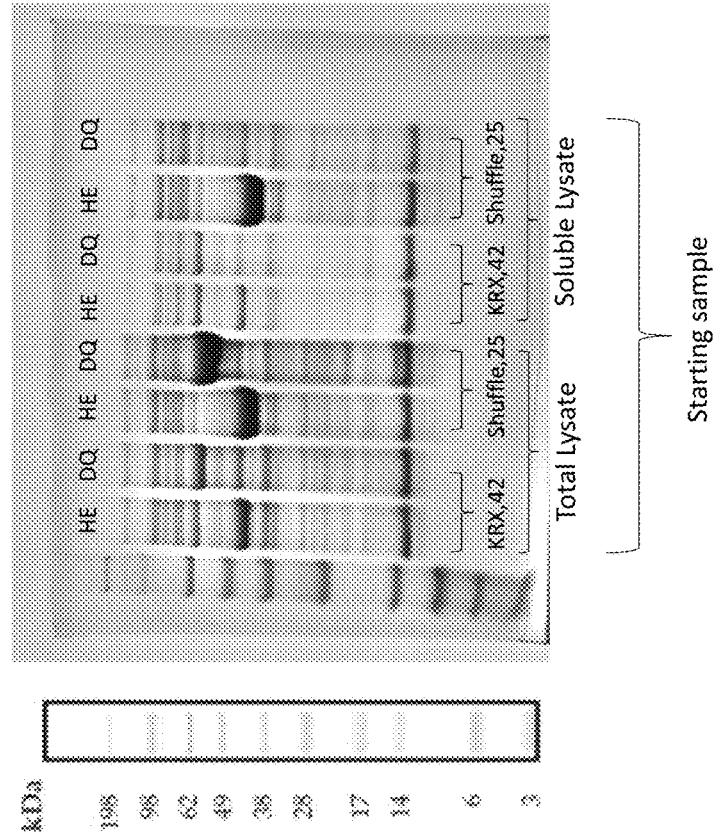
FIG. 9B is a digital image of another protein gel, showing purification performed by hand via use of an agarose-type bead.

FIG. 9A depicts a digital image of a protein gel, stained with Coomasie Blue, representing total lysate and a soluble fraction derived from total of holE (HE) and dnaQ (DQ). Each lane is noted to illustrate expression strain used, either New England Biolabs Shuffle® T7 Express (Shuffle), or Promega Single Step (KRX) cells, and the expression temperature used after induction. FIG. 9B is a digital image of another protein gel, stained with Pierce™ Silver Stain Kit (Thermo-Fisher), which represents purification performed by hand with Promega HaloLink beads (an agarose type bead). Contamination is indicated in the figure. Purification took approximately 10 hours for only two proteins, and the final product included contamination as indicated in FIG. 9B.

Example 2. Automated Protein Purification Using Two Types of Magnetic Beads

Figure 10:
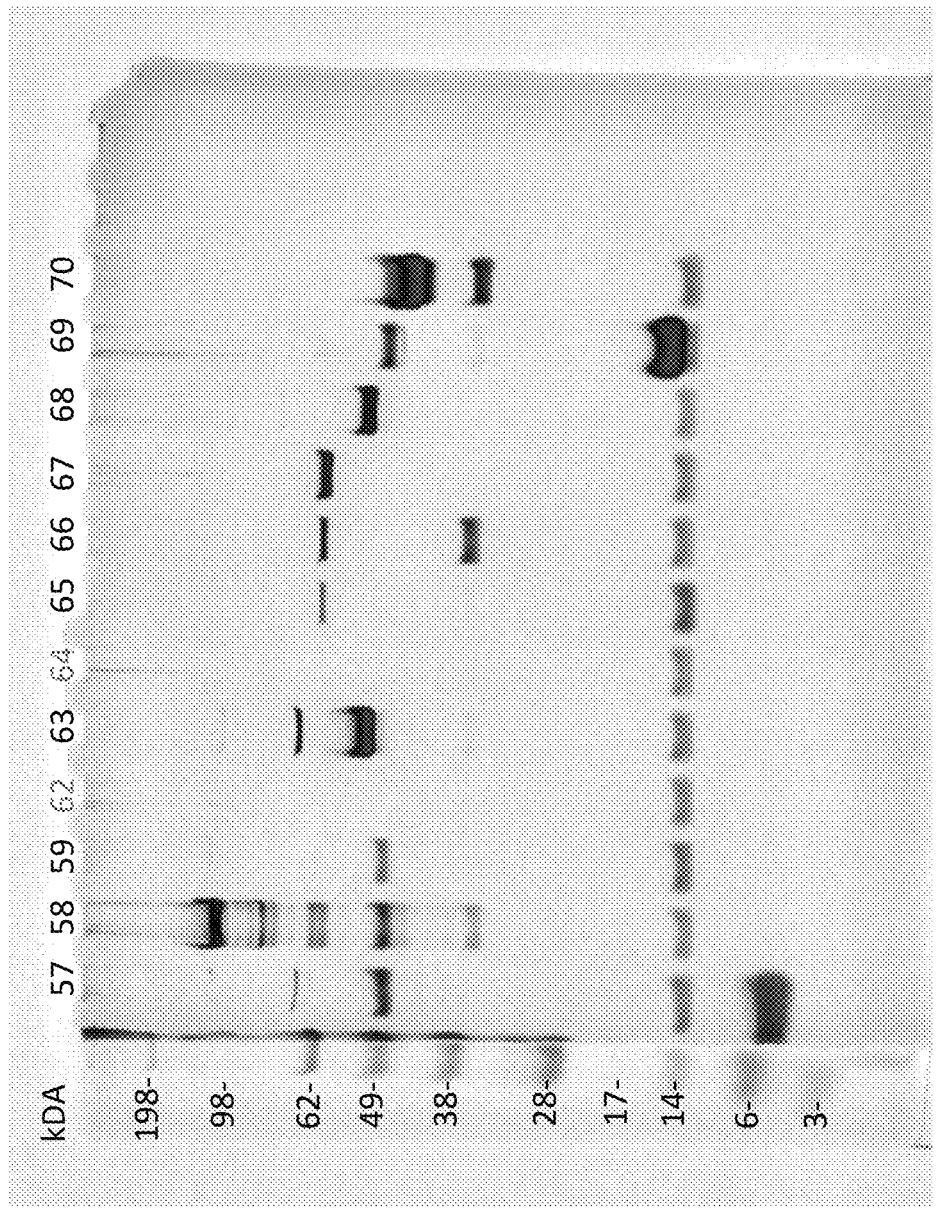
FIG. 10 is a gel illustrating purification of 12 different proteins via the methodology of FIG. 2.

This Example demonstrates rapid and effective purification of proteins using the automated purification methodology disclosed herein (see FIG. 2). 12 different tagged proteins were expressed in Shuffle at 25° C., and the proteins were purified according to the methodology disclosed herein with use of a ThermoFisher KingFisher™ Flex Automated Extraction Instrument. Specifically, tagged proteins were first bound to a first type of magnetic bead, and once bound, cleaved with a protease to liberate the protein from the magnetic beads. Next, a second type of magnetic bead was used to remove the protease, resulting in purified proteins. FIG. 10 is a protein gel illustrating the result of the purification scheme. Numerals 57, 58, 59, 62, 63, 64, 65, 66, 67, 68, 69, and 70 are used to show the 12 different protein samples. Samples 62 and 64 failed, but serve to illustrate a lack of background contamination. The purification of 12 different proteins took approximately 4 hours. The exact identity of the common contaminating band at approximately 14 KDa is unknown but may be a native E. coli dehalogenase (similar to the HaloTag): quantities of this contaminant were found to be negligible (e.g., near 0% of total sample purified according to mass spectroscopy).

Figure 11:
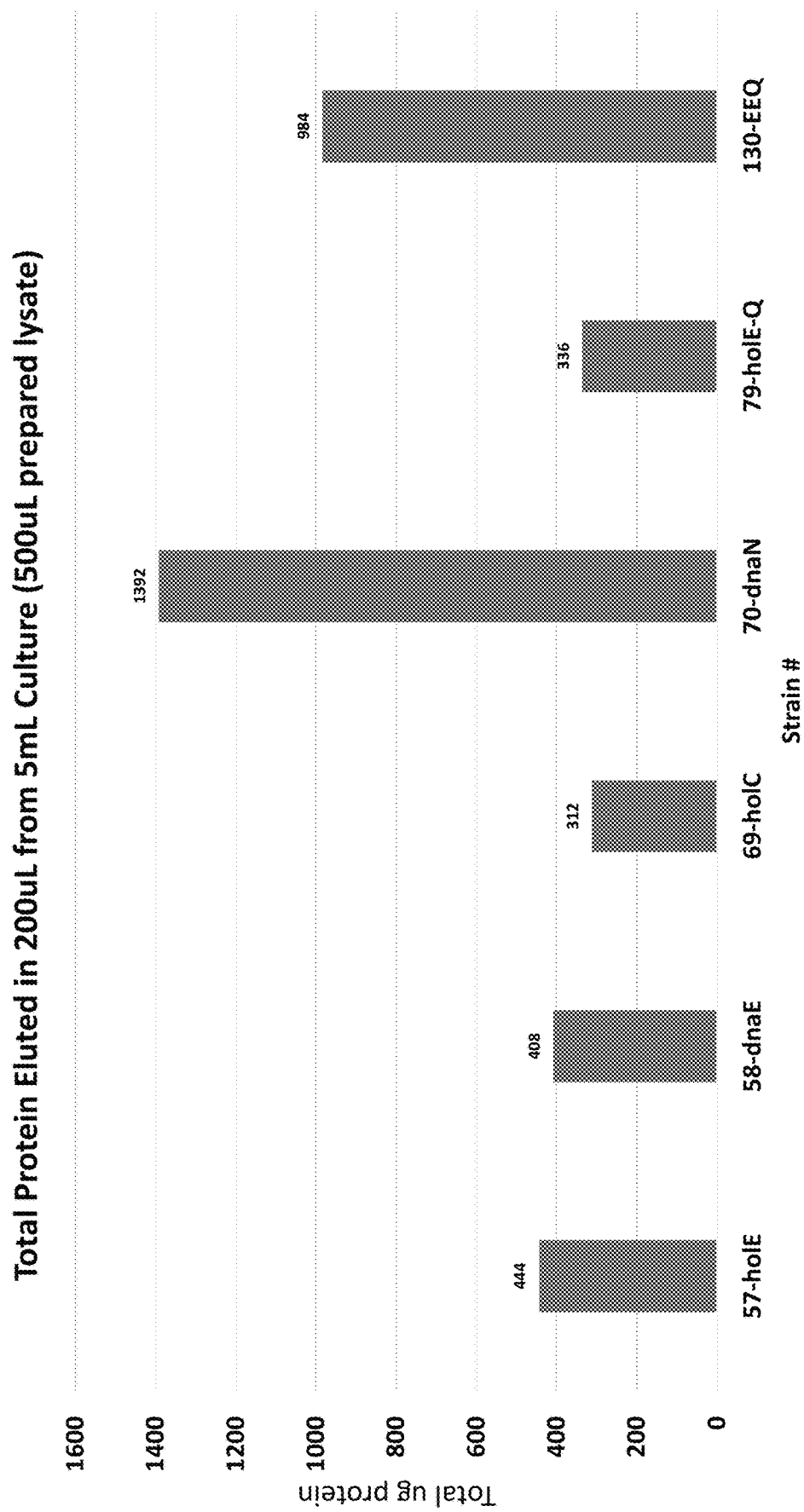
FIG. 11 is a graph showing total amount of protein obtained for selected proteins purified via the methodology of FIG. 2.
Figure 12:
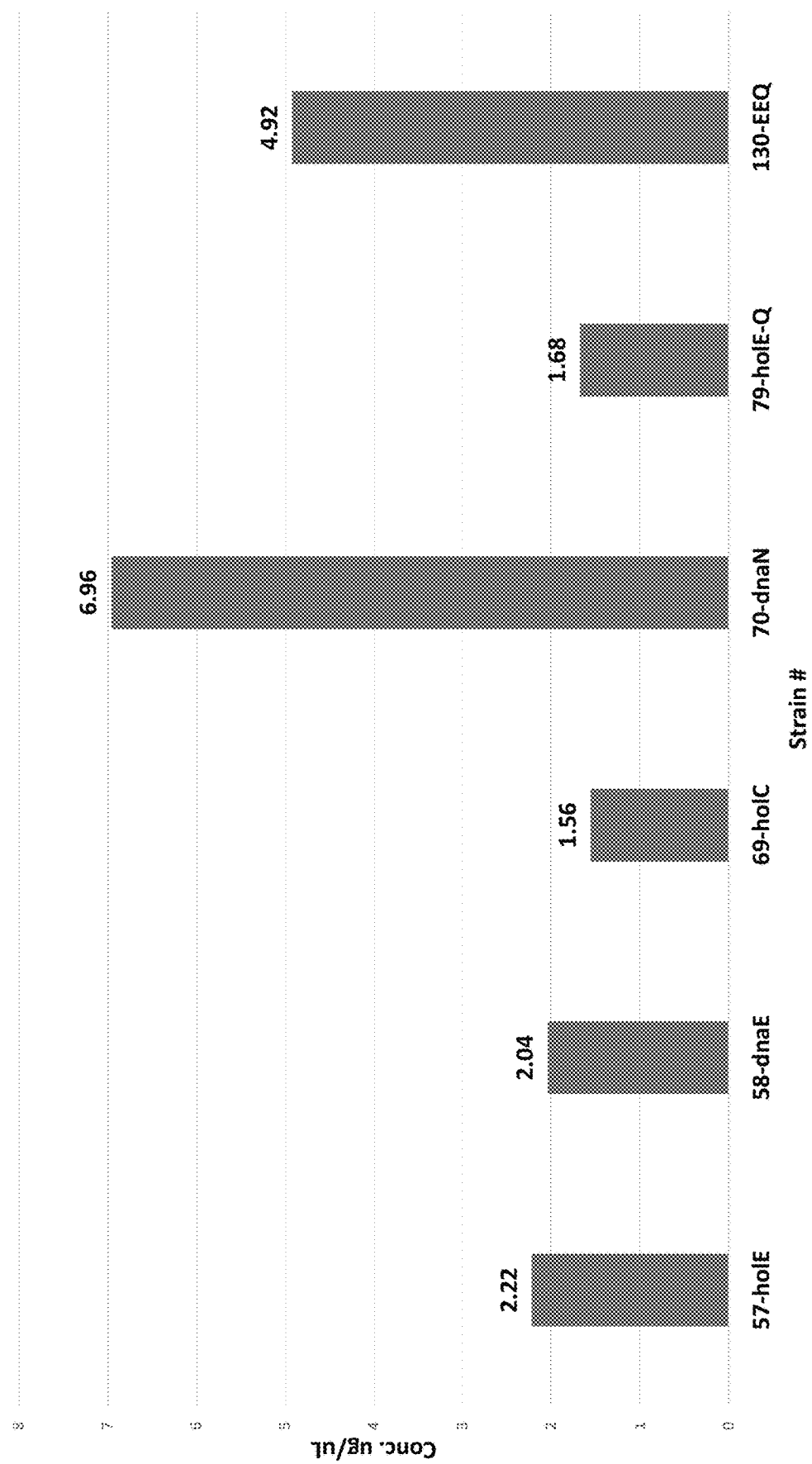
FIG. 12 is a graph showing concentration of protein obtained for selected proteins purified via the methodology of FIG. 2.

FIG. 11 illustrates total protein amounts purified from 5 mL starting culture, processed into a 500 μL lysate, and ultimately eluted into 200 μL as quantified by the Arizona State University Mass Spectroscopy facility. Samples chosen for quantitation (holE, dnaE, holC, dnaN, holE-Q, and EEQ) were those that were further analyzed by mass spectroscopy, discussed further below. The average obtained is 646 µg total protein. FIG. 12 illustrates protein concentration measurements from the samples (holE, dnaE, holC, dnaN, holE-Q (holE-dnaQ multiplexed protein), and EEQ (dnaE-holE-dnaQ multiplexed protein) purified from a starting culture volume of 5 mL, processed into a 500 µL lysate, and then eluted into 200 µL. The average concentration is 3.23 µg/µL. Increased yield and concentration can be obtained with increases in culture volume and the volume of magnetic beads used for purification.

Figure 13:
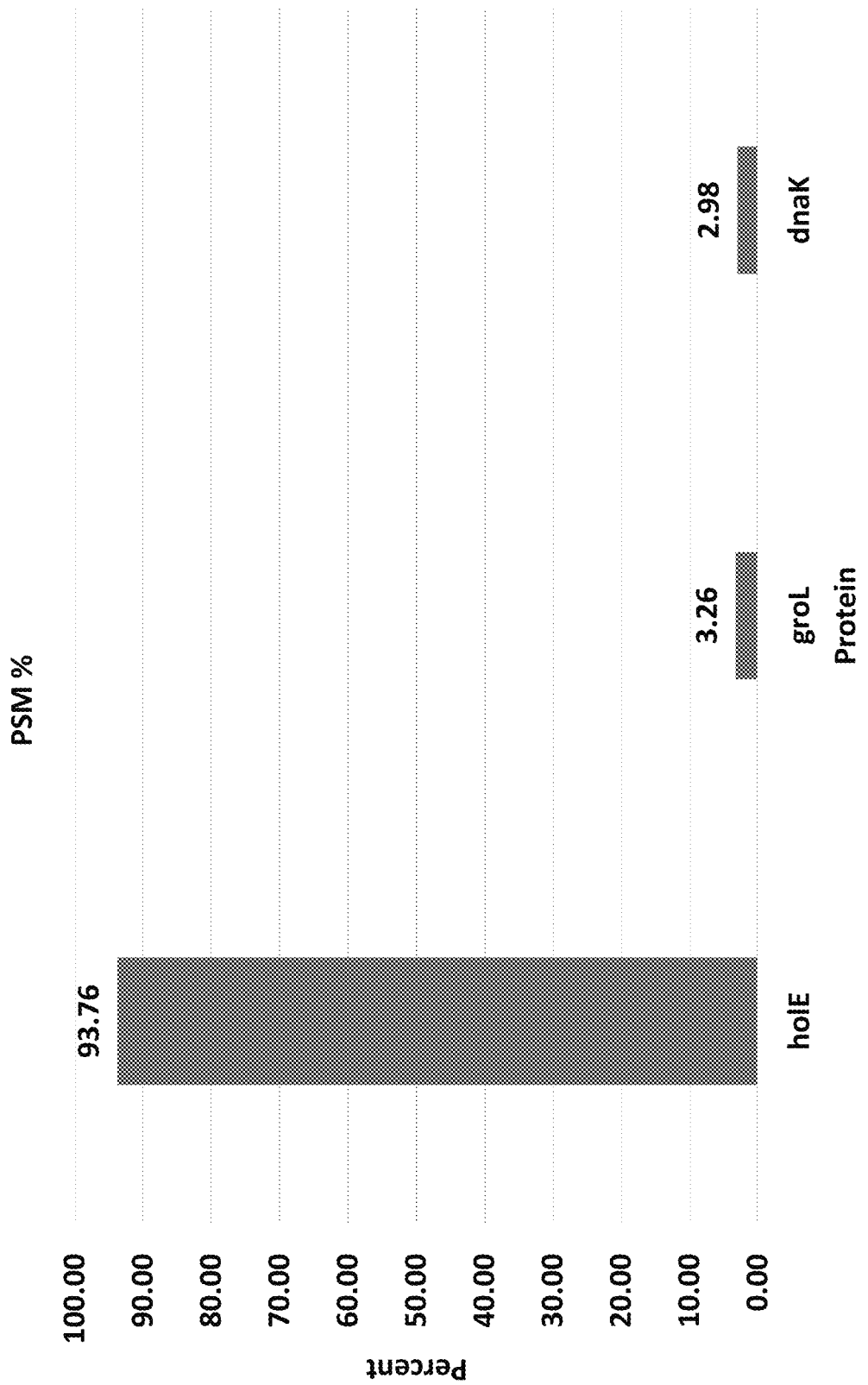
FIGS. 13-16 are graphs illustrating mass spectroscopy analysis using Protein Spectral Match percentage (PSM %) as an approximation of sample purity, for select proteins purified by the methodology of FIG. 2.
Figure 14:
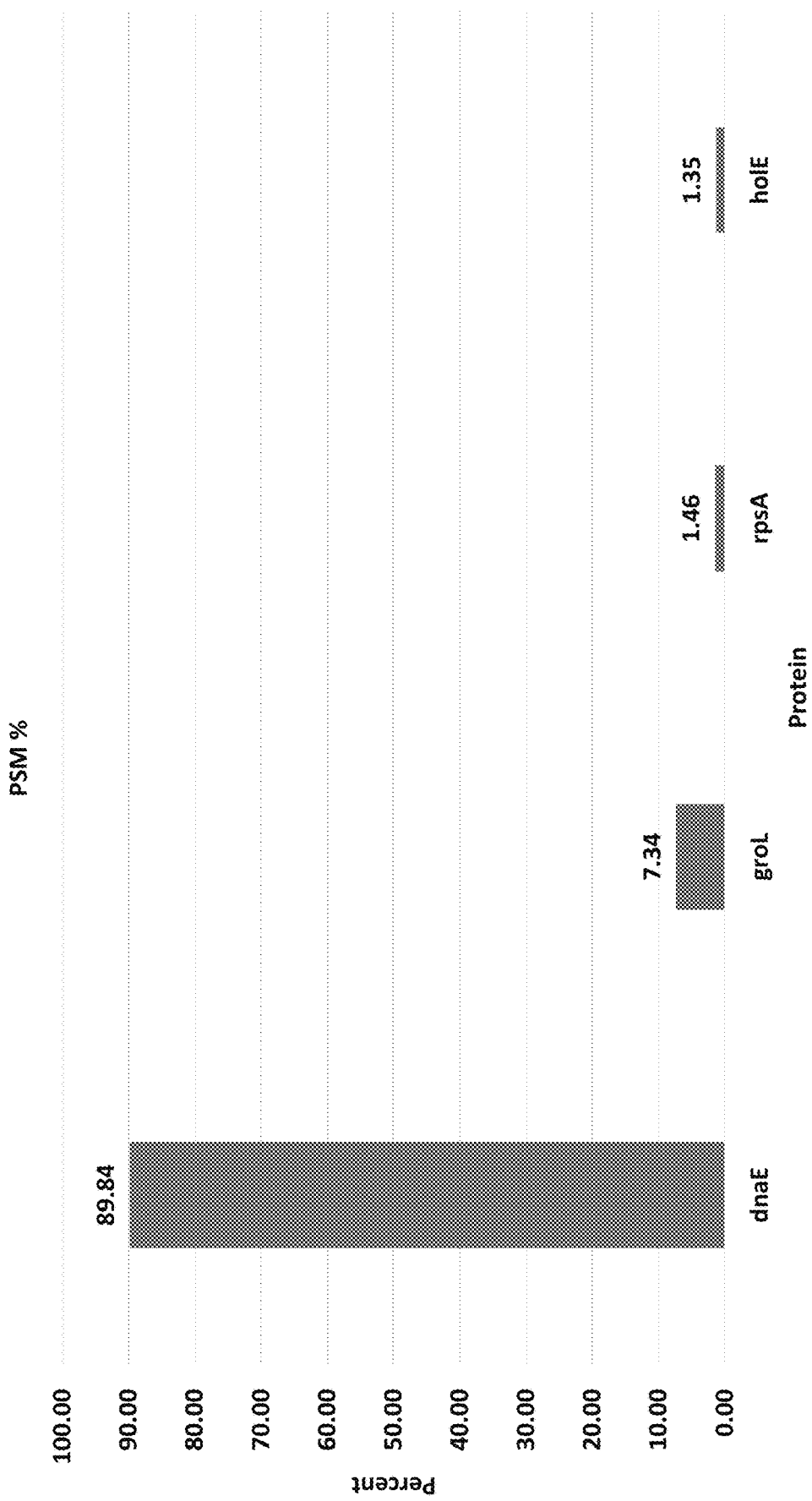
Figure 15:
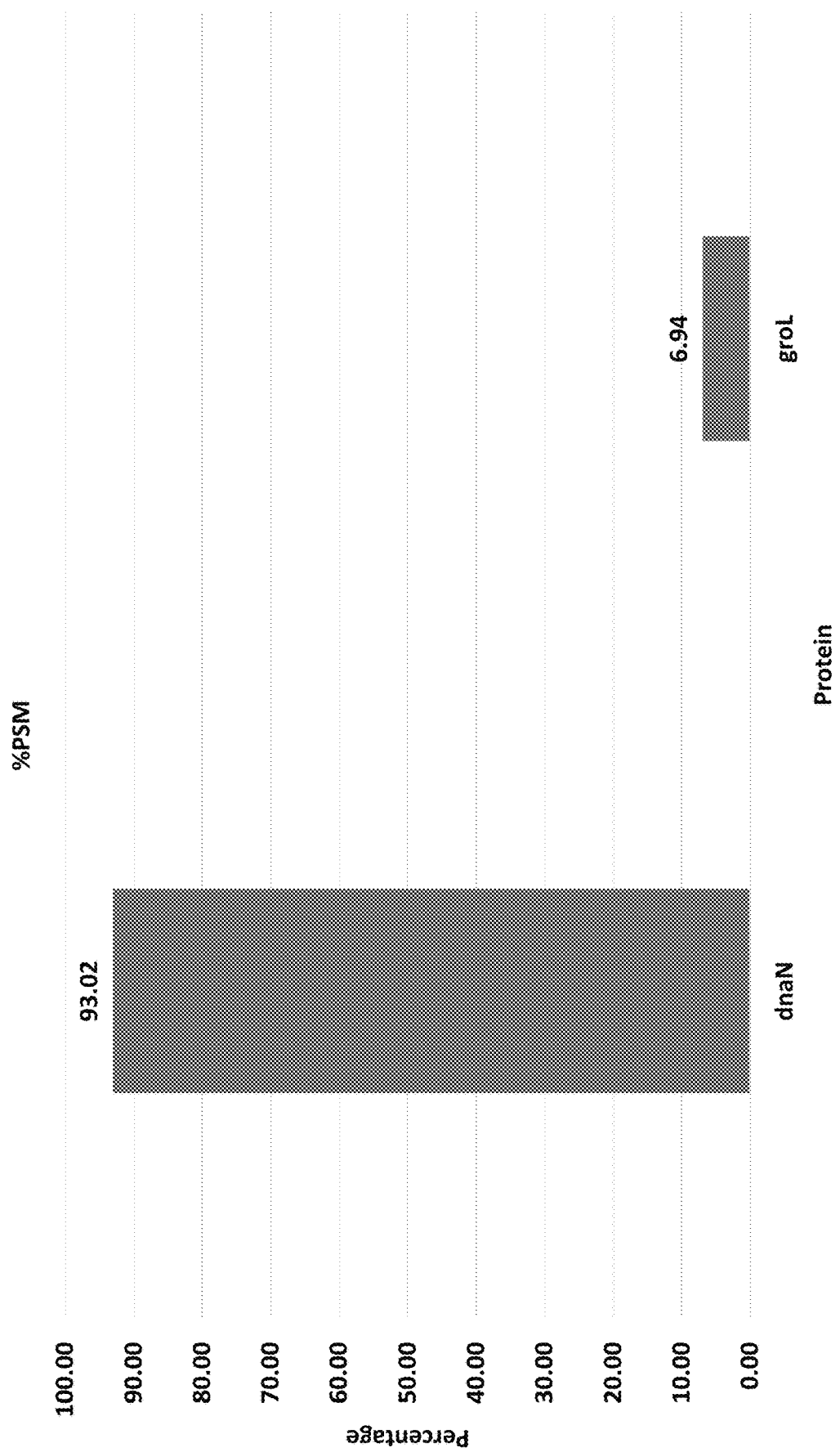
Figure 16:

Mass spectroscopy analysis using Protein Spectral Match percentage (PSM %) was employed as an approximation of sample purity. Turning to FIG. 13, the target protein holE was determined to be purified to 93.76% according to PSM %. FIG. 14 illustrates that dnaE was purified to 89.84% according to PSM %. FIG. 15 illustrates that dnaN was purified to 93.02% purity according to PSM %. FIG. 16 illustrates that holC was purified to 72.80% purity according to PSM. For the above examples pertaining to the use of PSM % as an approximation of sample purity, proteins in the raw data that represent less than 1% according to PSM % of the total are omitted.

Figure 17:
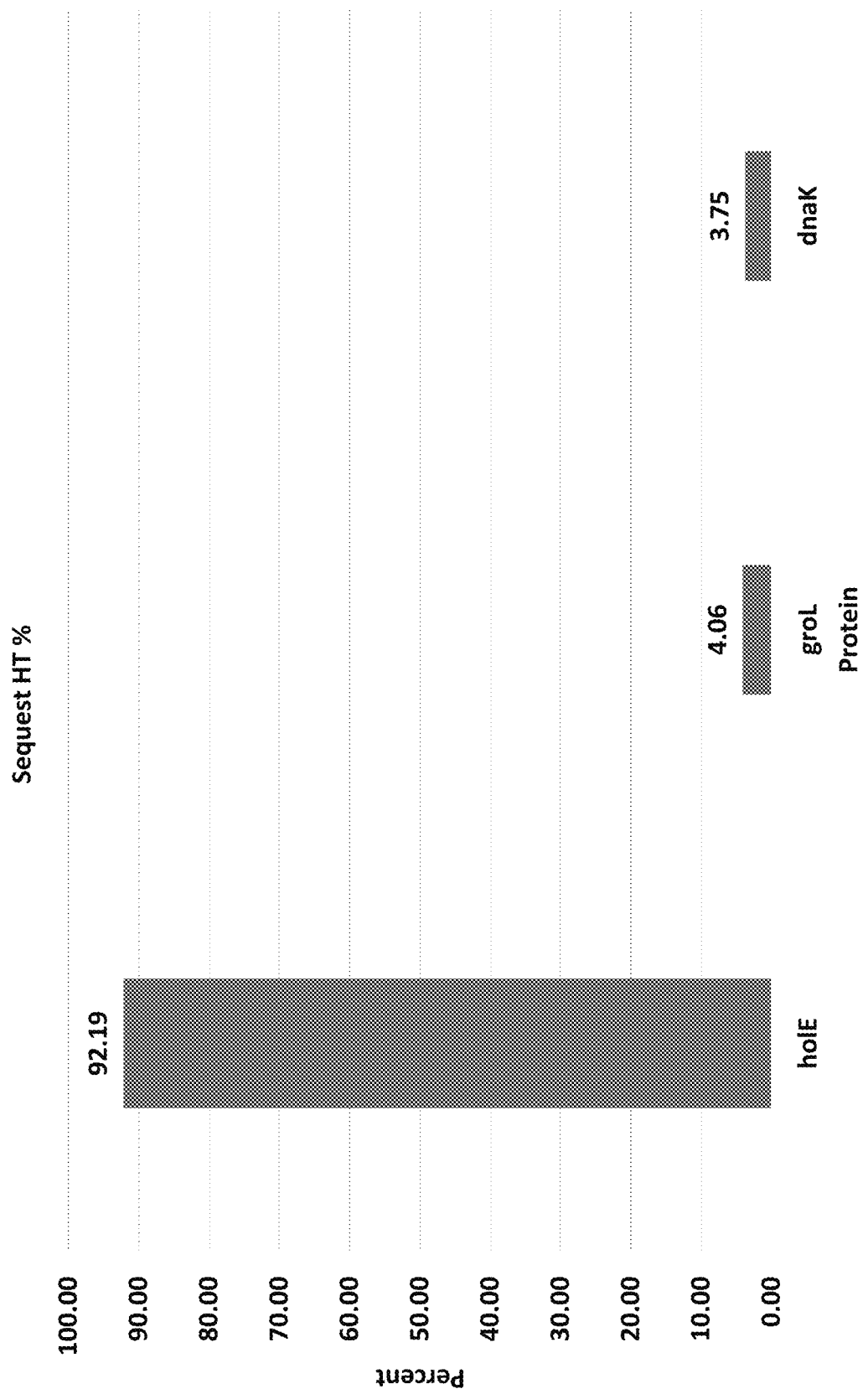
FIGS. 17-20 are graphs illustrating mass spectroscopy analysis using Sequest HT percentage (Sequest HT %) as an approximation of sample purity, for select proteins purified by the methodology of FIG. 2.
Figure 18:
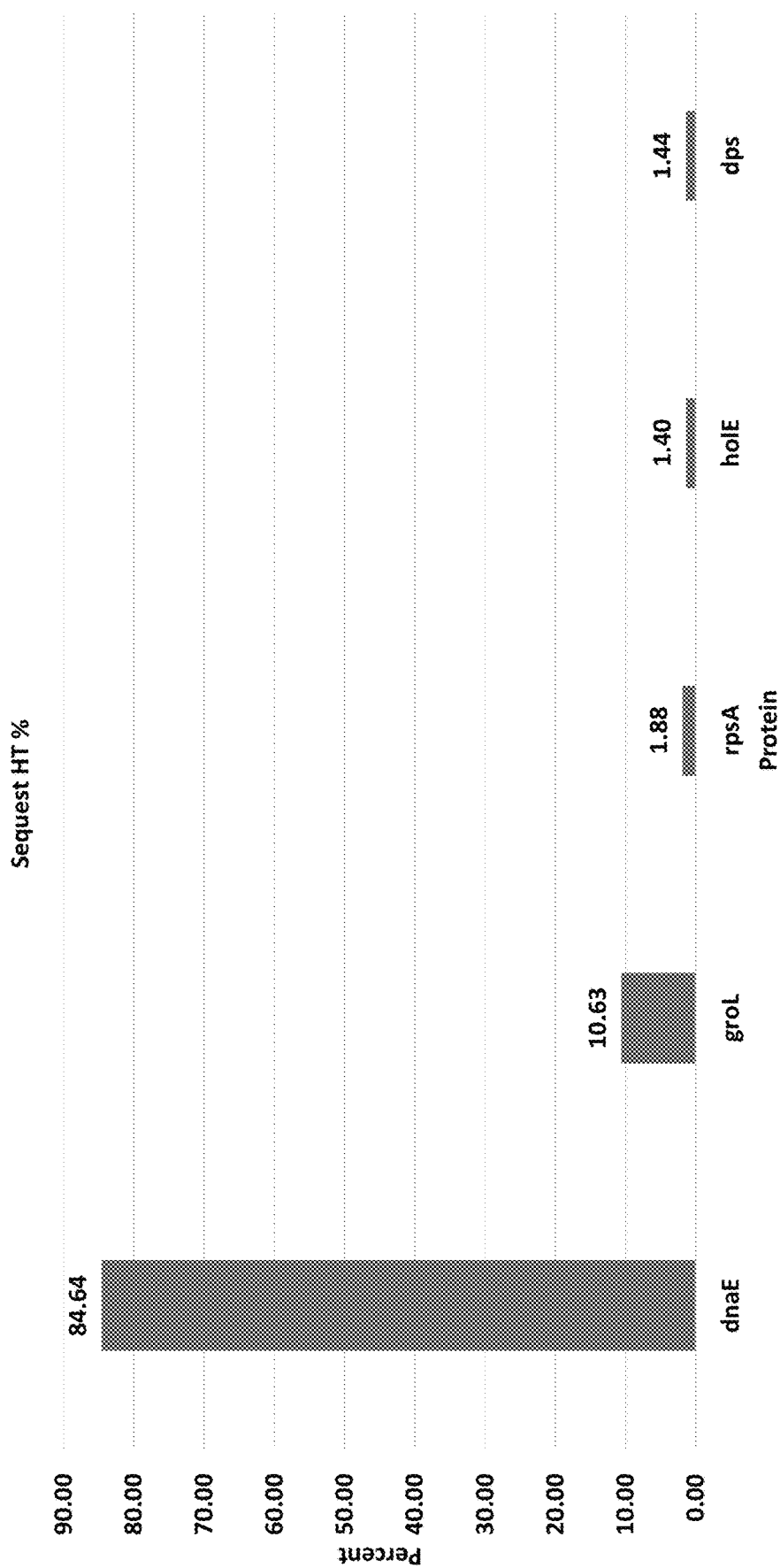
Figure 19:
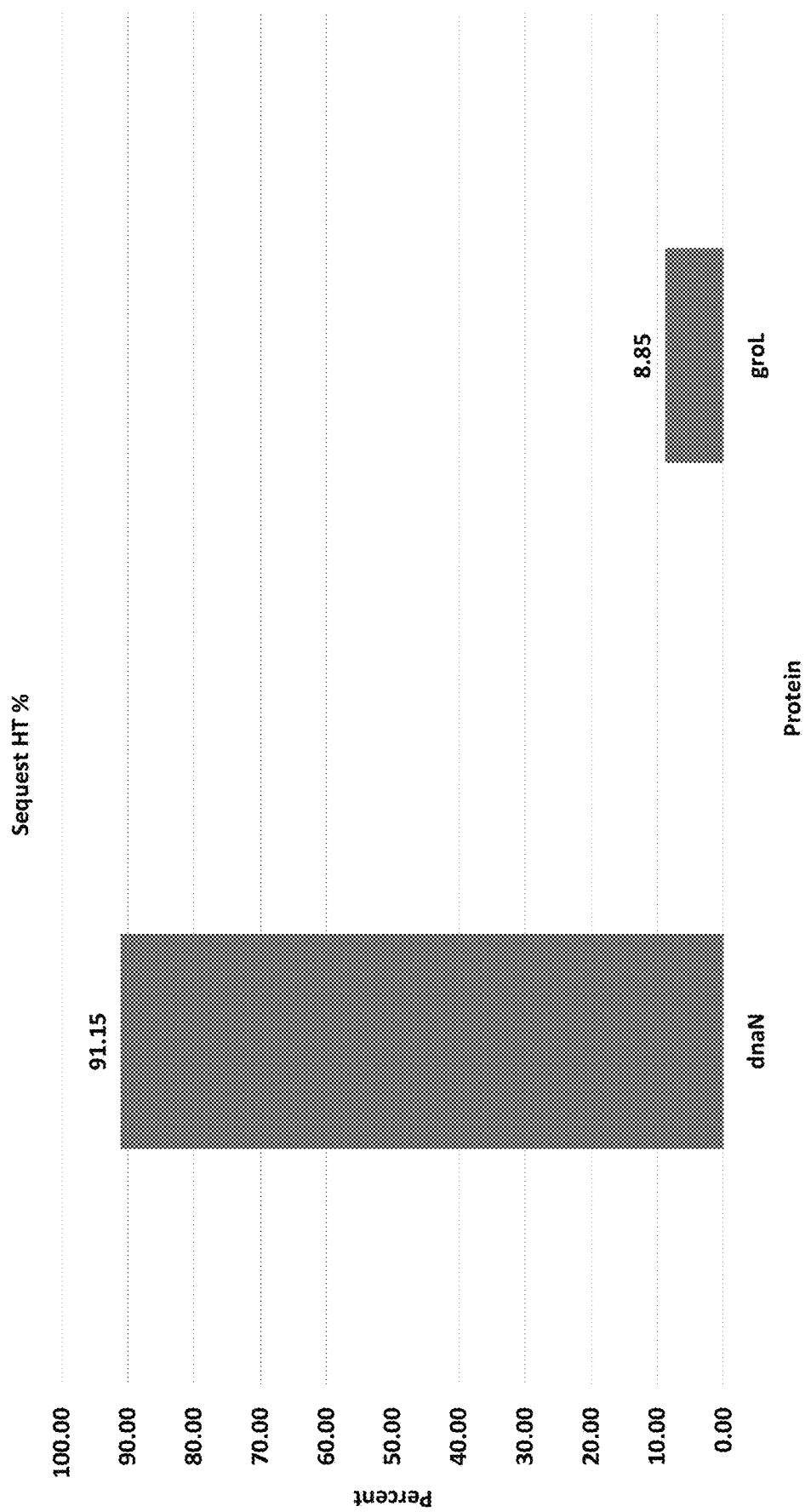
Figure 20:
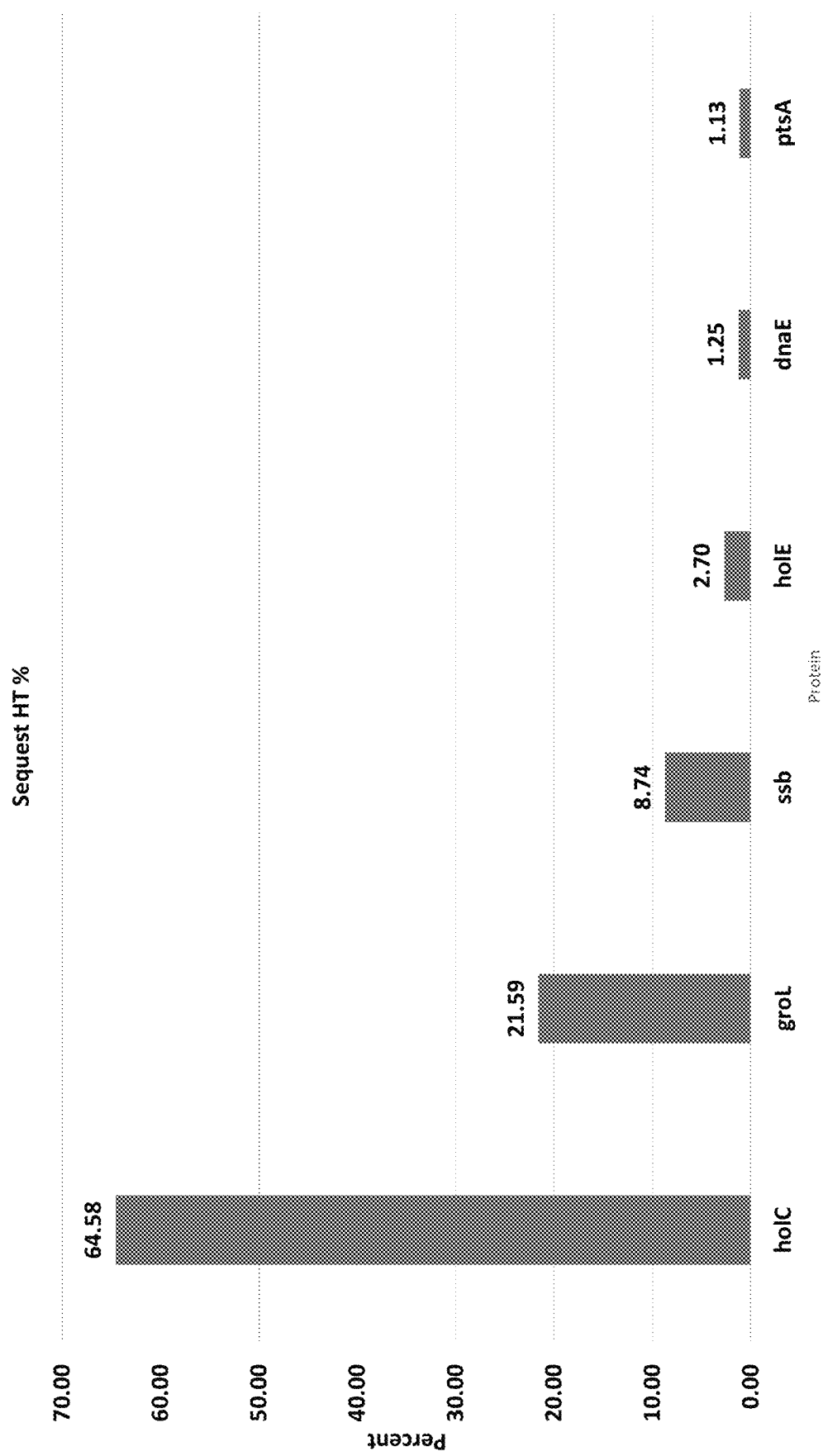

Mass spectroscopy analysis using Sequest HT percentage (Sequest HT %) was also employed as an approximation of sample purity. Sequest HT scores are calculated as the sum of all peptide cross-correlation values (Xcorr) above the specified score threshold. Xcorr score threshold is calculated as 0.8 multiplied by the peptide charge multiplied by the peptide relevance factor. Turning to FIG. 17, the target protein holE was purified to 92.19% purity according to Sequest HT %. FIG. 18 illustrates that the target protein dnaE was purified to 84.64% purity according to Sequest HT %. FIG. 19 illustrates that the target protein dnaN was purified to 91.15% purity according to Sequest HT %. FIG. 20 illustrates that the target protein holC was purified to 64.58% purity according to Sequest HT %. For the above examples pertaining to the use of Sequest HT % as an approximation of sample purity, proteins in the raw data that represent less than 1% according to PSM % of the total are omitted.

Example 3. Automated Purification of Protein Complexes

This Example demonstrates that the disclosed methodology of automated protein purification enables purification of multiple proteins from a single affinity tag. Automated protein purification in this Example was conducted via use of a ThermoFisher KingFisher™ Flex Automated Extraction Instrument.

Figures 21A, 21B:
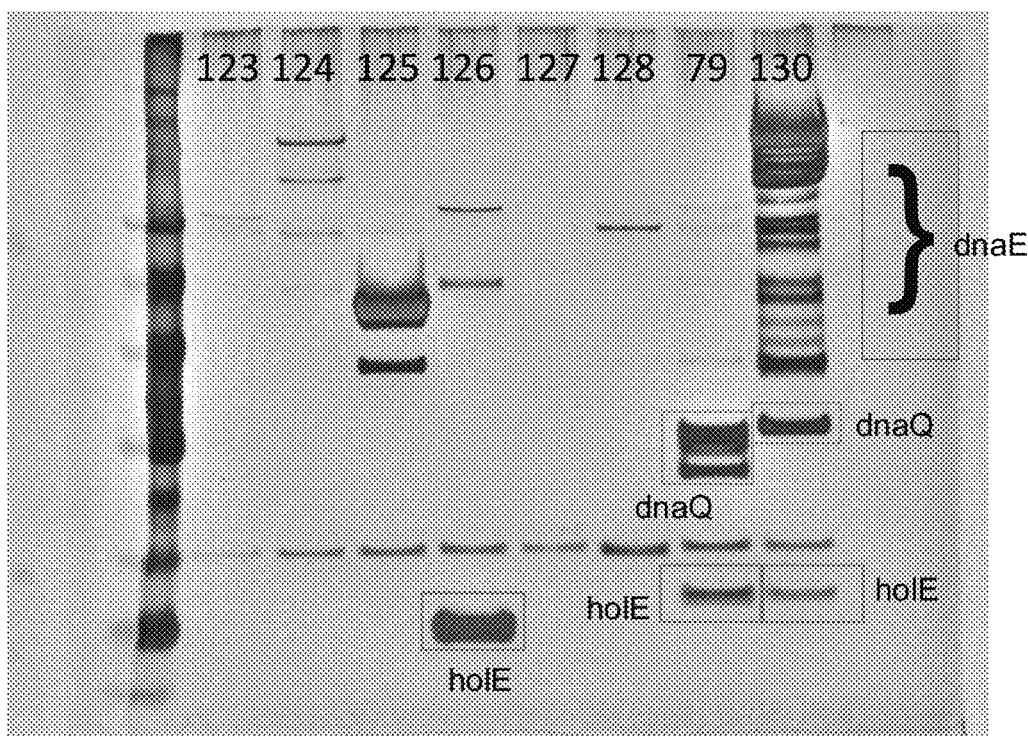
FIG. 21A depicts a protein gel showing purification of a single protein according to the methodology of FIG. 2, and purification of two proteins and three proteins according to the methodology of FIG. 3.
FIG. 21B is a table illustrating mass (kDa) of each of the proteins purified as shown in FIG. 21A.

FIG. 21A depicts a protein gel, stained with Pierce™ Silver Stain Kit (Thermo-Fisher, Waltham, MA). Lanes of interest are noted as 126 (holE), 79 (holE-dnaQ), and 130 (dnaE-holE-dnaQ), and correspond to the table illustrated at FIG. 21B. This gel illustrates single protein and single tag purification, as illustratively depicted in FIG. 2, and as shown in lane 126; two protein and single tag purification, as illustratively depicted in FIG. 3, and as shown in lane 79; and three protein and single tag purification, using similar methodology as that depicted in FIG. 3, and as shown in lane 130. Lane 130 has many proteins in the upper portion of the gel as expected. This protein, dnaE, is the central member of the *E. coli* DNA polymerase III, the genomic replicative polymerase. The holoenzyme fully assembled consists of 15 stably interacting proteins and transiently interacts with at least another 8 proteins that form their own complexes that may be made up of dimers, trimers, or higher order structures. dnaE alone was purified in FIG. 10, lane 58, for comparison. dnaE, holE, and dnaQ form the core complex of the DNA Polymerase III holoenzyme, and therefore naturally interact with each other. It was believed holE purified alone and dnaQ purified alone may be somewhat proteolytically degraded in vivo. This was evidenced by the holE band migrating at a slightly lower KDa than expected (see strain number 126). Once dnaQ was co-purified with holE (see strain number 79), the holE band began migrating at the expected KDa, though dnaQ continued to purify as a multiple band (indicative of potential degradation). dnaE was then co-purified with holE and dnaQ as a means to stabilize dnaQ, and indeed dnaQ began migrating as a single band indicating that it received some sort of proteolytic protection from dnaE. This protein gel illustrates the successful purification of two proteins from one tag, and three proteins from one tag according to the methodology illustratively shown in FIG. 3.

Figure 22:
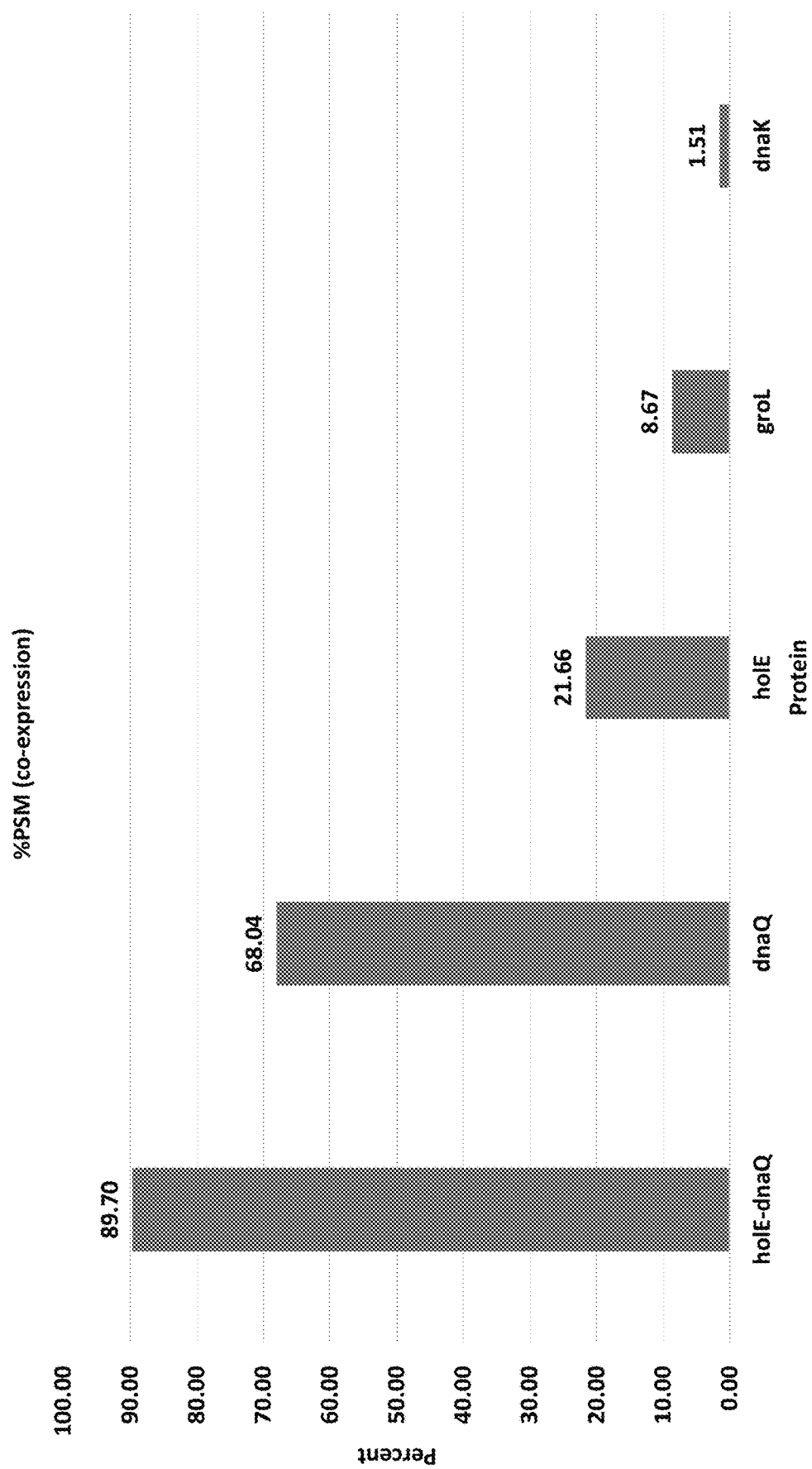
FIG. 22 is a graph illustrating mass spectroscopy analysis conducted using PSM % as an approximation of sample purity for two target proteins co-purified using the methodology of FIG. 3.
Figure 23:
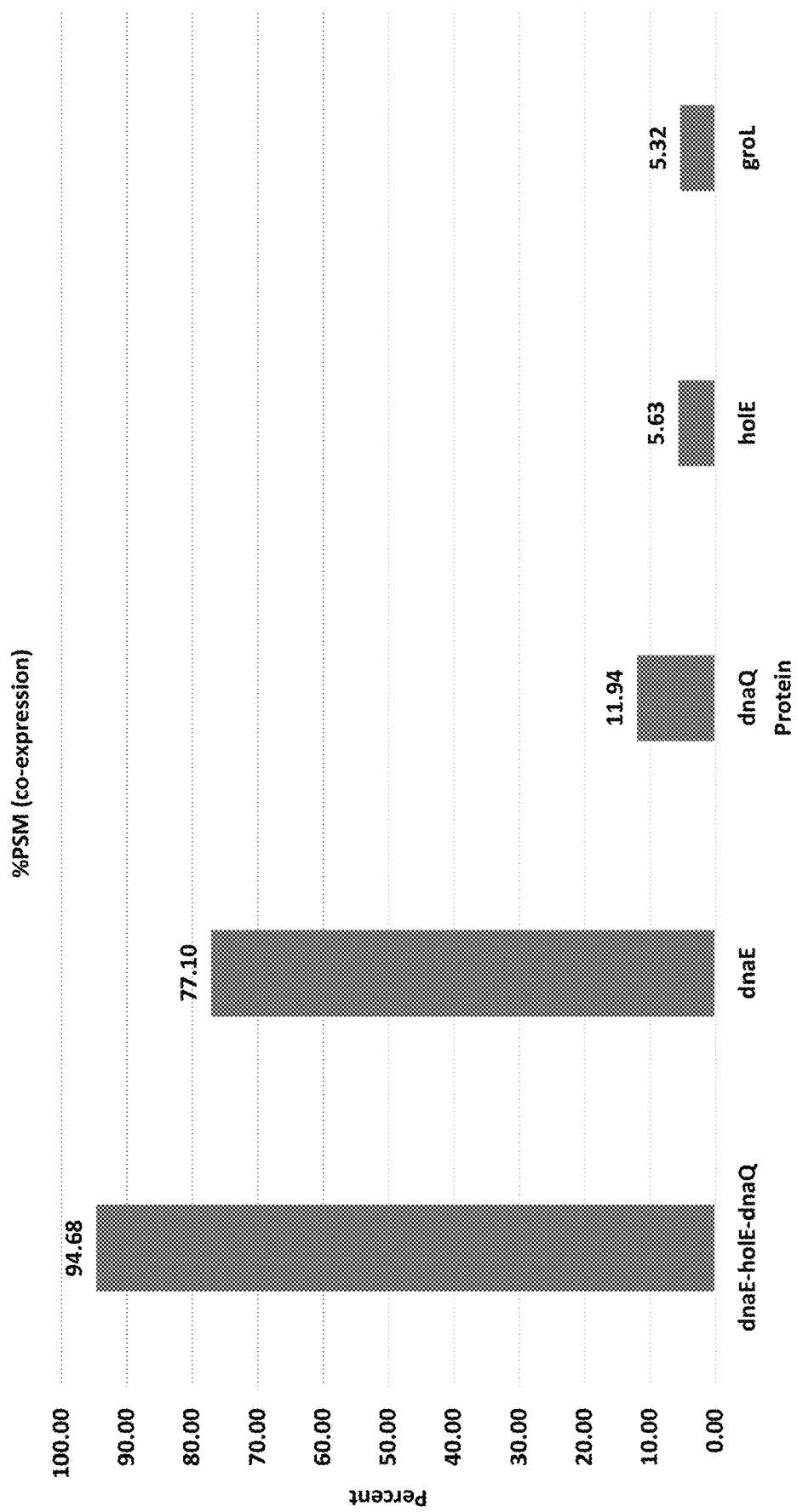
FIG. 23 is a graph illustrating mass spectroscopy analysis conducted using PSM % as an approximation of sample purity for three target proteins co-purified using methodology adapted from that of FIG. 3.

Mass spectroscopy analysis was conducted using PSM % as an approximation of sample purity. Target proteins holE and dnaQ were co-purified to 89.70% purity as described at FIG. 3 according to PSM % (FIG. 22). The holE-dnaQ column represents the addition of the two calculated values for each protein individually in the sample. Stoichiometry was expected to be 1:1 as the proteins are purified as a single polypeptide. However, when using PSM %, larger proteins may have more protein spectral matches as a consequence of their size. In another example, PSM % was used as an approximation of sample purity for co-purification of three proteins, the methodology of which is adapted from that exemplified at FIG. 3. FIG. 23 illustrates that target proteins dnaE, holE, and dnaQ were co-purified to 94.68% purity according to PSM %. The dnaE-holE-dnaQ column represents the addition of the three calculated values for each protein individually in the sample. Again, stoichiometry was expected to be 1:1 as the proteins are purified as a single polypeptide. However, as mentioned above, when using PSM %, larger proteins may have more protein spectral matches as a consequence of their size. For the above examples pertaining to the use of PSM % as an approximation of sample purity, proteins in the raw data that represent less than 1% according to PSM % of the total are omitted.

Figure 24:
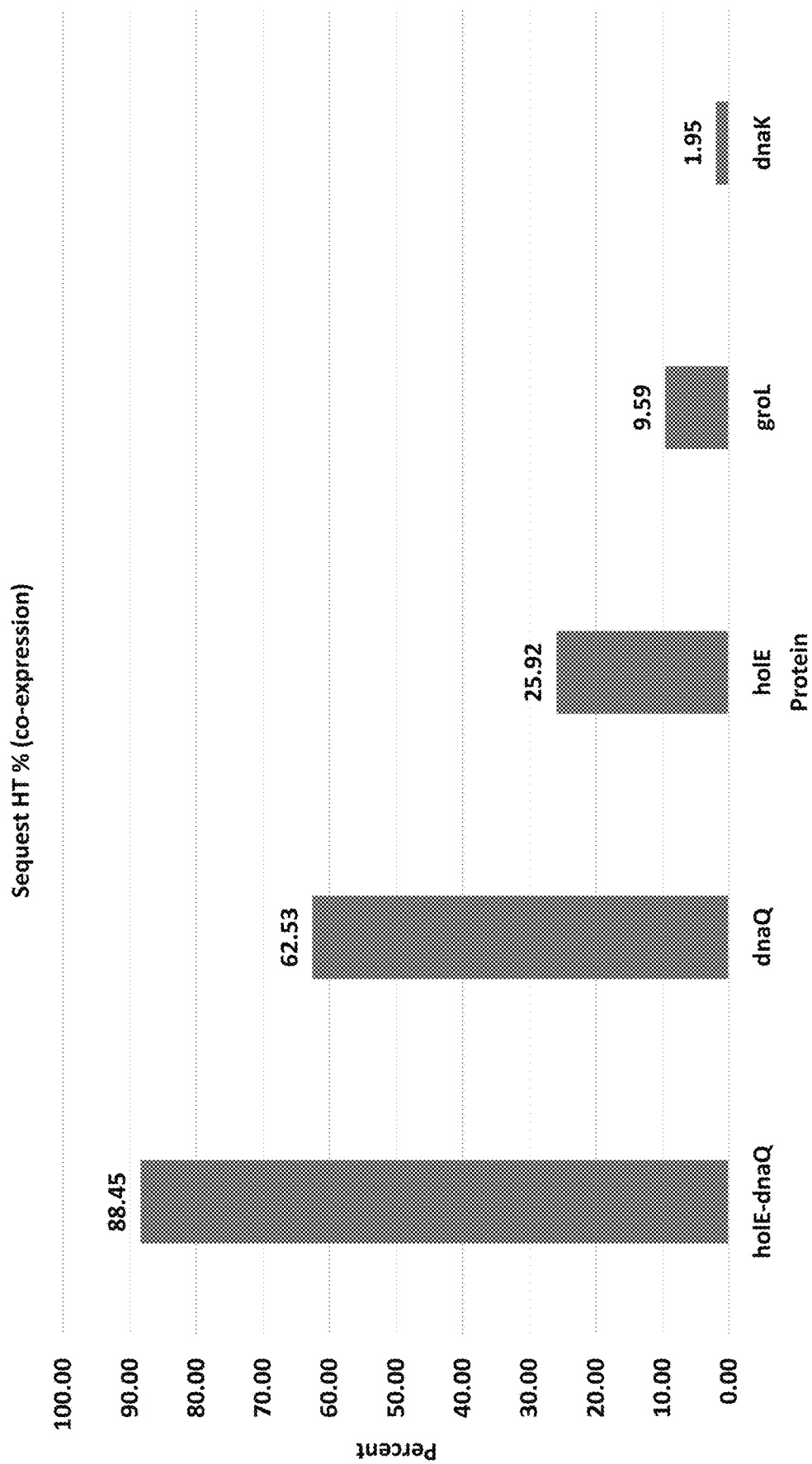
FIG. 24 is a graph illustrating mass spectroscopy analysis using Sequest HT % as an approximation of sample purity for two proteins co-purified using the methodology of FIG. 2.
Figure 25:
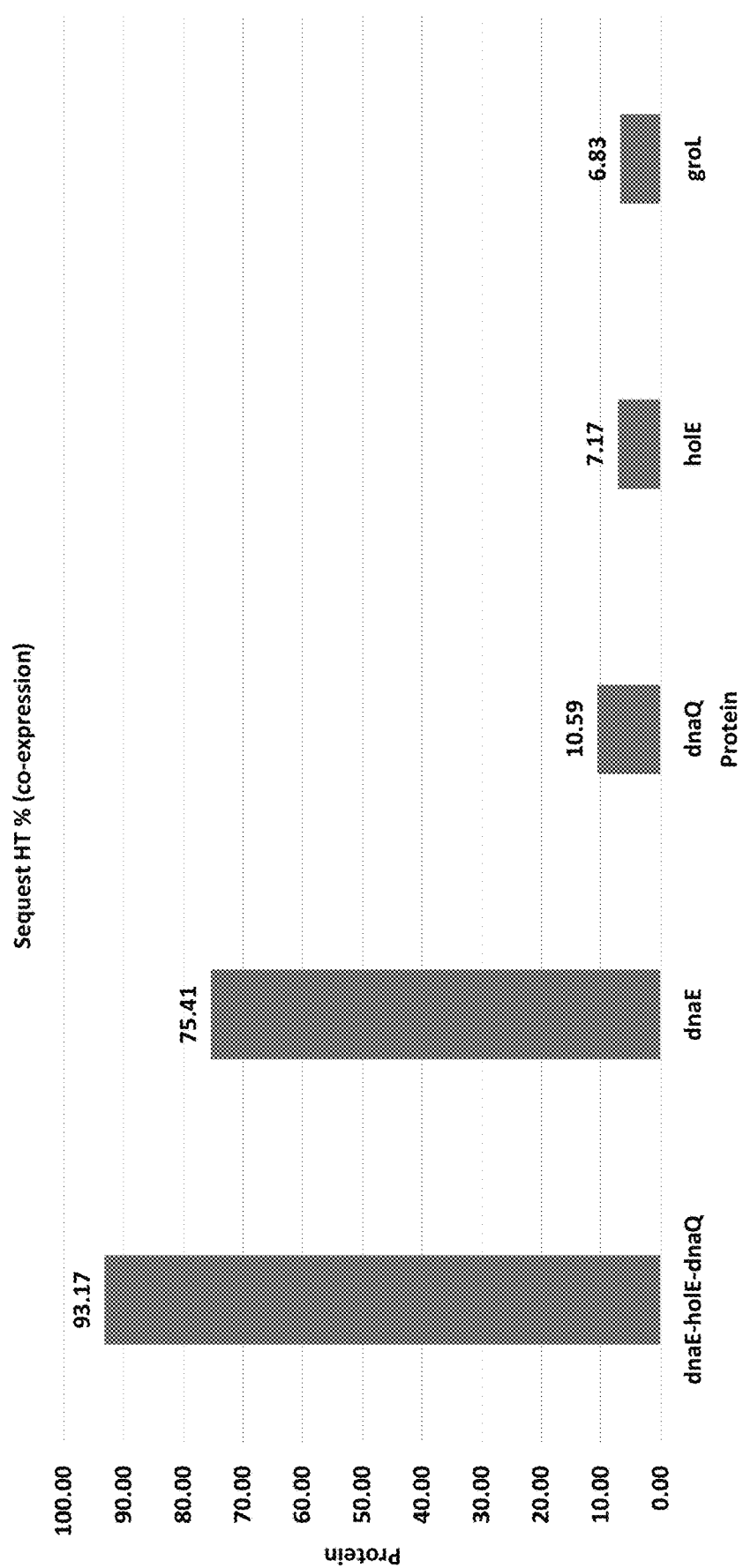
FIG. 25 is a graph illustrating mass spectroscopy analysis using Sequest HT % as an approximation of sample purity for three proteins co-purified using methodology adapted from that of FIG. 3.

Mass spectroscopy analysis using Sequest HT percentage (Sequest HT %) was also employed as an approximation of sample purity. As shown in FIG. 24, target proteins holE and dnaQ were purified to 88.45% purity according to Sequest HT % using methods described illustratively at FIG. 3. The holE-dnaQ column represents the sum of Sequest HT % values of holE and dnaQ individually. FIG. 25 illustrates that target proteins dnaE, holE, and dnaQ were purified to 93.17% purity according to Sequest HT % using methods adapted from that of FIG. 3. The dnaE-holE-dnaQ column represents the sum of Sequest HT % values of dnaE, holE, and dnaQ individually. With regard to the above examples pertaining to the use of Sequest HT % as an approximation of sample purity, proteins in the raw data that represent less than 1% according to PSM % of the total are omitted.

Example 4: Automated Purification of Viral Polymerase Subunit Proteins

Figures 26A, 26B:
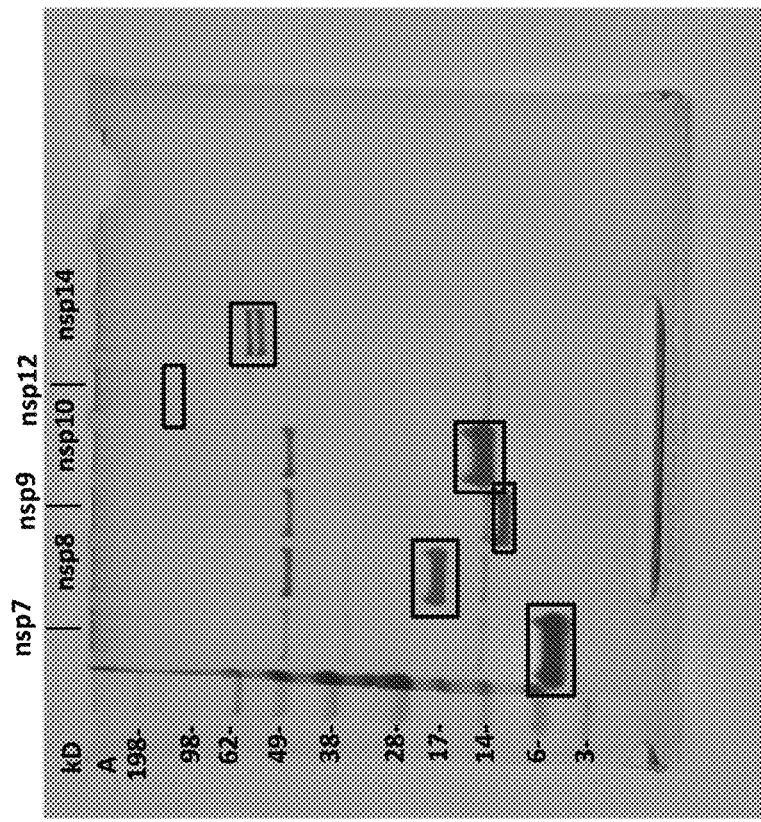
FIG. 26A is a protein gel illustrating purification of 6 different Covid-19 viral polymerase subunits in approximately 4 hours using the methodology of FIG. 2.
FIG. 26B is a table illustrating the mass of each of the 6 different proteins purified according to the methodology of FIG. 2, and as shown at FIG. 26A.

This Example demonstrates that the automated protein purification methodology disclosed herein can be used to rapidly purify viral subunit proteins from a bacterial expression host. FIG. 26A is a protein gel illustrating purification of Covid-19 viral polymerase subunit proteins from KRX (expressed at 25° C. Specifically, 6 tagged proteins were purified according to the disclosed methodology (FIG. 2) in approximately four hours. FIG. 26B is a table illustrating corresponding mass of each of the 6 proteins. One sample failed, noted as nsp12, but is illustrative of the lack of background protein contamination. The exact identity of the common contaminating band at approximately 14 kDa is unknown, but may be a native E. coli dehalogenase (similar to the HaloTag). Quantities of this contaminant were determined to be negligible (near 0% of total sample purified according to mass spectroscopy).

Materials and Methods Related to the Previous Examples

Cell Lysis by Freeze/Thaw

Cell pellets were resuspended completely in 500 μL Purification Buffer (50 mM HEPES/150 mM NaCl) per sample (culture volume 5 ml). To the resuspended cell pellets, 10 ul Lysozyme (100×, 10 mg/ml), 1 μl rlysozyme, 1 μl Benzonase Nuclease, and 11 μl Promega Protease Inhibitor Cocktail G6521 (50×, EDTA-free) (Promega Corporation, Fitchburg, WI) were mixed well and incubated on ice for 5-10 minutes. The cell suspension was then frozen in dry ice/ethanol bath for 2-5 minutes. It was then thawed in a water bath with occasional mixing. The above steps (minus the resuspension of cell pellets) were repeated for a total of 3 to 5 times. Optionally, to dissociate chaperonins from Halo Tag-target fusion protein, the following was added to the lysate: 1) ATP to a final concentration of 2 mM; 2) $MgSO_4$ or $MgCl_2$ to a final concentration of 10 mM, followed by incubation at 37° C. for 10 minutes. Immediately prior to purification, cell lysates were spun at 10,000-16,000 g for 15-30 minutes at 4° C. depending on target protein. In examples, more aggressive centrifugation (e.g., higher speeds and/or greater centrifugal force) can be used (protein dependent) to further reduce contaminant proteins. Supernatants were transferred to another tube and stored on ice until transfer to purification beads. A 10 μl aliquot of cell lysate was saved for analysis.

Other cell lysis methodologies are within the scope of this disclosure, including but not limited to sonication to disrupt cell membranes, chemical lysis (e.g., Bugbuster® Protein Extraction Reagent, Millipore Sigma, Burlington, MA), liquid homogenization (e.g., French Press), mechanical lysis (e.g., rotating blades that grind and disperse cells and tissues), and the like.

General Protocol for Using an Automated Extraction System (e.g., KingFisher™ Flex)

The following protocols are described generally with reference to use of an automated extraction system/bead mover device, such as the KingFisher™ Flex. The protocols described generally below were made with BindIt! Software of use on the Thermo-Fisher KingFisher™ Flex, however it is within the scope of this disclosure that other similar software and/or similar automated extraction systems may be used in accordance with the methodology herein disclosed. In this particular example, the bead mover device was the KingFisher™ Flex. Hence, the purification methodology was automated using a KingFisher™ Flex (Thermo Scientific Cat. no. 5400630, instrument software version 1.00.17, PC-Software Bindit, Version 3.3) in KingFisher™ Deep-well Blocks (KingFisher™ Accessory Kit B, MACHEREY-NAGEL GmbH & Co. K G, Düren, Ref.-Nr. 744951).

Briefly, to prepare magnetic beads for protein binding using an automated bead mover device, in embodiments five 96-well deep-well plates were prepared with various reagents. Volumes of reagents were dependent on initial cell culture volume (and limited by the volume of deep-well plate used (e.g., 96 well, or in some examples, 24-well). In embodiment where the desired target protein is expressed in 5 mL culture volumes, the plates were 1) a plate containing the tip-comb for protecting the magnetic head from the samples (referred to herein as the tip-comb plate), 2) a plate containing 275 μL/well of purification buffer (50 mM HEPES/150 mM NaCl) and 50 μL of magnetic beads meant to bind the protein of interest (referred to herein as wash 1 plate), 3) a plate containing 275 μL/well of purification buffer (referred to herein as wash 2 plate), 4) another plate containing 275 μL/well of purification buffer (referred to herein as wash 3 plate), and 5) a plate of 500 μL/well of cell lysate prepared via the freeze/thaw cell lysis method detailed above containing the tagged protein of interest (referred to herein as the bind lysate plate).

The automated protocol results in the automated bead mover device picking up the tip comb first from the tip comb plate. The wash 1 plate was placed into position beneath the magnetic head of the bead mover device. Mixing can occur when the magnetic head/rod are in a separated position (refer to illustration at FIG. 1D), which can enable just the plastic tips of the tip combs to move up and down within the individual wells. In embodiments, the mixing was allowed to proceed at high speed for 1 minute. After mixing was finished, the magnetic heads were lowered into the tip combs, and the head is further lowered into the bottom of the plate. Magnetic beads were collected for a total of 30 seconds.

Next, the magnetic head is programmed to rise above the plate after the beads have collected on the exterior of the tip comb, and the wash 2 plate was moved into position beneath the magnetic head. The magnetic heads were then lowered into the wash 2 plate, and the magnetic head was programmed to move independent of the plastic tip comb to separate (refer to FIG. 1D), which resulted in the magnetic beads being released into respective wells of the wash 2 plate. Mixing was performed at high speed for one minute, followed by collection of the magnetic beads for 30 seconds. The magnetic head was programmed to then rise out of the wash 2 plate with the beads collected on the exterior of the tip comb, and the wash 3 plate was moved into position. The automated bead mover was programmed to then release the beads into the appropriate wells of the wash 3 plate, and the washing was programmed to occur at high speed for one minute before the beads were once again collected by the magnetic heads. Once collected, the magnetic head was programmed to rise out of the wash 3 plate.

Next, the automated bead mover was programmed to move the bind lysate plate into position. It may be understood that the above-discussed steps correspond to equilibration of the magnetic beads used in the purification methodology. Hence, with the magnetic beads equilibrated, the automated bead mover was programmed to release the equilibrated beads into the cell lysate (bind lysate plate) containing the tagged protein of interest. In embodiments, the beads were mixed with the lysate for one hour at a slow speed, although longer or shorter timeframes and various speeds are encompassed by the present disclosure.

While the step of binding of beads to the tagged protein was occurring, seven new plates were prepared as follows: 1) wash 1a plate (400 μL/well purification buffer), 2) wash 2a plate (300 μL/well purification buffer), 3) wash 3a plate (200 µL/well purification buffer), 4) wash 4a plate (200 µL purification buffer), 5) wash 5a plate (100 µL purification buffer), 6) disposal plate (100 µL purification buffer), and 7) cleavage plate (empty). The cleavage plate was left empty as cleavage solution was needed to be added at a pause step during the protocol by the user, as the cleavage solution was made fresh before addition. The cleavage solution contained the protease specific to the protease recognition site between the tag and the protein of interest. For TEV, a concentration of 300 units per milliliter was used (and is recommended) for this procedure. As mentioned herein, any protease used may include a unique affinity tag to facilitate removal of the protease at a later step.

Responsive to the step of binding the tagged protein to the magnetic beads being complete, the program caused the automated bead mover to transfer the magnetic beads with bound protein via the magnetic heads to wash 1a plate, where the solutions in individual wells were mixed for 10 minutes at slow speed. Following the mixing/washing, the magnetic beads were transferred to the wash 2a plate via the magnetic heads, and were again mixed/washed for 10 minutes before the magnetic beads were collected and transferred to the wash 3a plate. The same general procedure was then repeated for each of the wash 3a plate, wash 4a plate, and wash 5a plate.

Following the step corresponding to wash 5a plate, the program caused the automated bead mover to pause. As mentioned, the pause step was included to allow for a user to pipette 100 µL of the cleavage solution into appropriate wells of the cleavage plate. The program then caused the magnetic beads to be collected from the wash 5a plate (e.g., collected for 30 seconds), and were then moved and released into the cleavage plate where the magnetic beads were mixed in the solution for 1.5 hours. Following the mixing, the program caused the beads to be collected again, and transferred to the dispose plate where they were released thereto.

The program included another pause step following the transfer of the magnetic beads to the dispose plate. This second pause step was included to allow the user to add magnetic clean-up beads to the cleavage plate to remove the protease. As discussed above, the clean-up magnetic beads included a recognition element specific to the affinity tag included as part of the protease. In examples, 10 µL of clean-up beads was used (and is recommended), although other volumes greater than or less than 10 µL is within the scope of this disclosure. It may be understood that in example methodology as detailed above at FIGS. 5A-5B, additional clean-up magnetic beads may be utilized that include a recognition element specific to an affinity tag comprising a non-covalent tag located on an opposing terminus of the protein compared to the covalent tag.

The automated bead mover was programmed to mix the clean-up beads with the solution for 20 minutes at a slow speed, following collection of the clean-up beads for 30 seconds. Once the clean-up beads were collected via the magnetic heads, they were released into the wash 5a plate as they were no longer needed. The tip comb was then released into the bind lysate plate, and the protocol ends. The purified protein remained in the corresponding wells of the cleavage plate.

The above-discussion regarding the programming of the automated bead mover was based on the methodology discussed with regard to FIGS. 2-3, but was adapted for other purification schemes corresponding to the disclosed methods. One skilled in the art can modify the above-mentioned program based on their needs (e.g., longer or shorter wash times, additional wash steps, elution steps, speeds at which mixing occurs, and the like).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for purification of a target protein fused to an affinity tag, comprising:
   contacting a sample comprising the target protein with a plurality of type 1 magnetic beads capable of recognizing and binding the affinity tag under conditions sufficient for the plurality of type 1 magnetic beads to bind to the affinity tag fused to the target protein in the sample, wherein a protease cleavage sequence is between the affinity tag and the target protein;
   washing the plurality of type 1 magnetic beads to remove contaminating material from the sample;
   contacting the sample with a cleavage solution containing an endoprotease that cleaves the cleavage sequence to release the target protein from the plurality of type 1 magnetic beads;
   contacting the sample with a plurality of type 2 magnetic beads capable of recognizing and binding to the endoprotease under conditions sufficient to bind the endoprotease in the sample, wherein the type 2 magnetic beads do not bind the affinity tag fused to the target protein; and
   removing the plurality of type 1 magnetic beads and the plurality of type 2 magnetic beads, thereby purifying the target protein.

2. The method of claim 1, wherein washing the plurality of type 1 magnetic beads further comprises:
   contacting the plurality of type 1 magnetic beads that are bound to the affinity tag fused to the target protein with a magnet under conditions sufficient to bind the plurality of type 1 magnetic beads to the magnet; and
   transferring the plurality of type 1 magnetic beads that are bound to the affinity tag fused to the target protein to one or more wash solutions to facilitate removal of contaminating material from the sample; and
   subsequent to the washing, releasing the plurality of type 1 magnetic beads from the magnet.

3. The method of claim 1, further comprising:
   removing the plurality of type 1 magnetic beads from the sample prior to contacting the sample with the plurality of type 2 magnetic beads.

4. The method of claim 1, wherein contacting the sample with the plurality of type 2 magnetic beads occurs without prior removal of the plurality of type 1 magnetic beads from the sample.

5. The method of claim 1, wherein the affinity tag fused to the target protein is a first affinity tag; and
   wherein the protease cleaves the target protein from the first affinity tag, thereby releasing the target protein from the plurality of type 1 magnetic beads, while the first affinity tag remains bound to the plurality of type 1 magnetic beads.

6. The method of claim 5, wherein the plurality of type 2 magnetic beads bind to the endoprotease by way of a second affinity tag fused to the endoprotease.

7. The method of claim 6, wherein the first affinity tag and the second affinity tag are different.

8. The method of claim 5, wherein the target protein is comprised of two or more different proteins; and
   wherein the endoprotease further cleaves the target protein into the two or more different proteins.

9. The method of claim 1, wherein the method does not include any centrifugation steps.

10. The method of claim 1, wherein the method does not involve use of any detergent.

* * * * *